United States Patent
Lü et al.

(10) Patent No.: US 6,800,590 B2
(45) Date of Patent: Oct. 5, 2004

(54) 2-PYRIMIDINYLOXY-N-ARYL-BENZYLAMINE DERIVATIVES, THEIR PROCESSES AND USES

(75) Inventors: Long Lü, Shanghai (CN); Jie Chen, Hangzhou (CN); Jun Wu, Hangzhou (CN); Wen Ling, Shanghai (CN); Lisheng Mao, Shanghai (CN); Mingzhi Li, Hangzhou (CN); Xian Cai, Shanghai (CN); Weili Peng, Hangzhou (CN); Yong Wu, Shanghai (CN); Shenggan Wu, Hangzhou (CN); Hongjun Wang, Shanghai (CN); Guochao Wang, Hangzhou (CN); Hu Cui, Shanghai (CN); Shidong Han, Hangzhou (CN); Weilian Qiu, Shanghai (CN); Yonghua Wang, Hangzhou (CN)

(73) Assignees: Shanghai Institute of Organic Chemistry, Shanghai (CN); Chinese Academy of Sciences, Shanghai (CN); Zheijiang Chemical Industry Research Institute, Hangzhou (CN)

( * ) Notice: Subject to any disclaimer, the term of this patent is extended or adjusted under 35 U.S.C. 154(b) by 0 days.

(21) Appl. No.: 10/380,865
(22) PCT Filed: Sep. 13, 2001
(86) PCT No.: PCT/CN01/01395
§ 371 (c)(1), (2), (4) Date: Apr. 9, 2003
(87) PCT Pub. No.: WO02/34724
PCT Pub. Date: May 2, 2002

(65) Prior Publication Data
US 2003/0220198 A1 Nov. 27, 2003

(51) Int. Cl.[7] .......................... A01N 43/54; C07D 239/34
(52) U.S. Cl. .................. 504/242; 504/243; 544/300; 544/301; 544/310; 544/312; 544/316

(58) Field of Search ..................... 544/316, 310, 544/312, 300, 301; 504/242, 243

(56) References Cited

FOREIGN PATENT DOCUMENTS

EP    0 468 695 A1    1/1992

*Primary Examiner*—Richard L. Raymond
(74) *Attorney, Agent, or Firm*—Welsh & Katz, Ltd.

(57) ABSTRACT

This invention relates to new 2-pyrimidinyloxy-N-aryl-benzylamine derivatives, their preparation processes and uses as chemical herbicides in agriculture. The compound has the following structure:

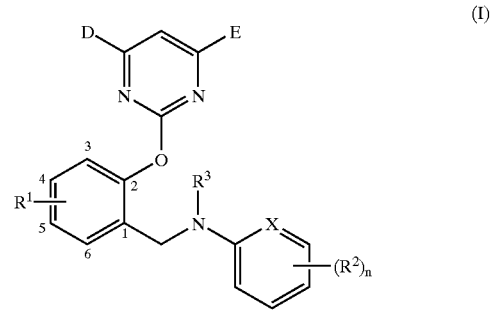

wherein, D or E is hydrogen, halogen, $C_1$–$C_4$ alkyl, $C_1$–$C_4$ alkoxy, $C_1$–$C_4$ haloalkyl or $C_1$–$C_4$ haloalkoxy; $R^1$ is hydrogen, halogen, $C_1$–$C_4$ alkyl, $C_1$–$C_4$ alkoxy; $R^2$ is hydrogen, halogen, $C_1$–$C_4$ alkyl, $C_1$–$C_4$ alkoxy, $C_1$–$C_4$ carbamyl, $C_1$–$C_4$ alkoxycarbonyl, $C_1$–$C_4$ haloalkyl, cyano, nitro, carboxy or its alkali metal, alkali earth metal and organoammonium salts, $C_1$–$C_4$ alkylamido, $C_1$–$C_4$ haloalkylamido, heterocyclic amido, benzamido or substituted benzamido, benzo or substituted benzo compounds; $R^3$ is hydrogen, $C_1$–$C_4$ alkanoyl, $C_1$–$C_4$ haloalkanoyl, benzoyl or $C_1$–$C_4$ alkoxyacetyl; X is CH or N; n=1–3.

10 Claims, No Drawings

2-PYRIMIDINYLOXY-N-ARYL-BENZYLAMINE DERIVATIVES, THEIR PROCESSES AND USES

This application is a national stage filing of PCT/CN01/01395, filed Sep. 13, 2001.

TECHNICAL FIELD

The present invention relates to new 2-pyrimidinyloxy-N-aryl-benzylamine derivatives, their preparation processes and uses as chemical herbicides in agriculture.

BACKGROUND ART

Agricultural chemicals are the indispensable productive materials for human to obtain provisions, to stably produce grain mass with good harvest. In recent hundred years, agricultural chemicals such as insecticides, bactericides, herbicides and the like made a great contribution to human beings. Recently, as the population of the world continues growing, the need of people to provisions is continuously increasing. However, the increasing rate of plowland can not be kept with the growing rate of population. In order to solve the cosmopolitan problem, we must rely on increasing crop yield per unit area and improving the quality of crops. It is necessary to apply various means such as breeding, arable farming, fertilizing and the like. Of those, the use of agricultural chemicals is an essential one of these means. However, it should also be seen that while agricultural chemicals made a great contribution to human civilization, high toxic, high residual agricultural chemicals also bring along negative effect on the environment which human beings rely on because of the knowledge limitation of human to agricultural chemicals. It is the direction of developing new agricultural chemicals to develop high efficient, low toxic, degradable, safe and environmental friendly agricultural chemicals instead of those low efficient, high toxic, high residual and high resistant ones.

It is reported in references that pyrimidinyloxy benzene derivatives can be used as chemical herbicides, for example, in Agr. Biol. Chem., vol. 30, p 896 (1966), JP 79-55729, U.S. Pat. Nos. 4,248,619 and 4,427,437. Recently, on the basis of pyrimidinyloxy benzene derivatives, a class of compound with excellent weeding activity, pyrimidine salicylic acid derivatives, is found, such as in EP 223,406; 249,708; 287,072; 287,079; 315,889; 321,846; 330,990; 335,409; 346,789; 363,040; 402,751; 435,170; 435,186; 457,505; 459,243; 468,690; 658,549 and 768,034; JP 04368361; GB 2,237,570; DE 3,942,476, etc. Of those, the representative examples are Pyrithiobac-sodium (KIH-2031, EP 315,889), Bispyribac-sodium (KIH-2023, EP 321,846), Pyriminobac-methyl (KIH-6127, JP 04,368,361), Pyribenzoxim (EP 658549) and Pyriftalid (EP 768,034). The action mechanism thereof is the same as that of sulfonyl urea herbicides, both of them are inhibitors of acetyl lactic acid synthetase (ALS), destroying the synthesis of amino acid such as valine, leucine and isoleucine within plant bodies. Although pyrimidine salicylic acid derivatives have very high weed control activity, currently they are only suitable to weed control in cotton field and paddy field.

OBJECTIVES OF THE PRESENT INVENTION

An objective of the present invention is to provide a 2-pyrimidinyloxy-N-aryl-benzylamine derivative.

Another objective of the present invention is to provide a process for preparing 2-pyrimidinyloxy-N-aryl-benzylamine derivative.

One further objective of the present invention is to provide the use of 2-pyrimidinyloxy-N-aryl-benzylamine derivative as an effective active ingredient in herbicides.

SUMMARY OF THE PRESENT INVENTION

The present invention relates to a 2-pyrimidinyloxy-N-aryl-benzylamine derivative. One target compound, 2-pyrimidinyloxy-N-aryl-benzylamine, is prepared in the following way: firstly, reacting salicylal with an aromatic amine to produce intermediate (II), secondly, reducing the intermediate (II) to afford the corresponding intermediate (III), and finally, further reacting the intermediate (III) with 2-methylsulfonyl (i.e. $CH_3SO_2$-)-4D,6E-substituted pyrimidine in the present of a base to produce the target compound. The reaction between the target compound and an acid anhydride or acid chloride compound in the presence of a base can produce another target product, i.e., N-acylated product of 2-pyrimidinyloxy-N-aryl-benzylamine. The compound of the present invention is an active ingredient in herbicides, which can be formulated into various liquor, oil solutions, emulsions, powder preparations, granule preparations or capsule preparations, etc. and applied to weed control of crops such as rape, cotton, paddy, soybean and the like.

DISCLOSURE OF THE INVENTION

The 2-pyrimidinyloxy-N-aryl-benzylamine derivatives of the present invention are represented by the following structure (I):

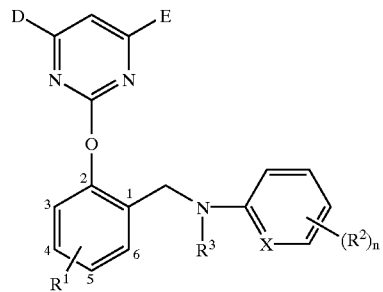

where:

D and E can be same or different, and each independently represents hydrogen, halogen, $C_1$–$C_4$ alkyl, $C_1$–$C_4$ alkoxy, $C_1$–$C_4$ haloalkyl or $C_1$–$C_4$ haloalkoxy, particularly both of D and E are methoxy.

$R^1$ is hydrogen, halogen, $C_1$–$C_4$ alkyl, $C_1$–$C_4$ alkoxy, which can be at any one position of 3-, 4-, 5-, 6-positons in benzene ring.

$R^2$ is hydrogen; halogen; $C_1$–$C_4$ alkyl; $C_1$–$C_4$ alkoxy; $C_1$–$C_4$ carbamyl; $C_1$–$C_4$ alkoxycarbonyl; $C_1$–$C_4$ haloalkyl, particularly trifluoromethyl; cyano; nitro; carboxy or its alkali metal, alkali earth metal and organoammonium salts; $C_1$–$C_4$ alkylamido; $C_1$–$C_4$ haloalkylamido, particularly trifluoromethylamido; benzamido or substituted benzamido (substituents can be halogen, $C_1$–$C_4$ alkyl, $C_1$–$C_4$ alkoxy, trifluoromethyl, cyano, nitro, etc. located at m-, o- or p-position); heterocyclic amido, such as, for example, pyridine, thiophene, thiazole, pyrimidine, etc; $R^2$ can be located at m-, o- or p-position of a benzene ring (n=1–3), or be a benzo or substituted benzo compound, preferably, $R^2$ is a halogen monosubstituting at m-, o- or p-position of a benzene ring; methyl; methoxy; trifluoromethyl; $C_1$–$C_4$ alkoxycarbonyl; $C_1$–$C_4$ carbamyl; carboxy or its sodium, potassium or ammonium salts; $C_1$–$C_4$ alkylamido; benzamido or substituted benzamido; heterocyclic amido and the like.

$R^3$ is hydrogen, $C_1$–$C_4$ alkanoyl, $C_1$–$C_4$ haloalkanoyl, benzoyl and $C_1$–$C_4$ alkoxyacetyl. $R^3$ is preferably being hydrogen, acetyl, chloroacetyl, dichloroacetyl, benzoyl or methoxyacetyl, particularly hydrogen.

X is H or N, preferably H.

Next, the typical compounds the present invention involves are listed in Table 1.

TABLE 1

2-pyrimidinyloxy-N-aryl-benzylamine derivatives

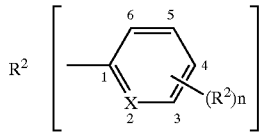

| Compound No. | D=E | $R^1$ | $(R^2)n$ | $R^3$ | X |
|---|---|---|---|---|---|
| I-1 | OCH$_3$ | H | H | H | H |
| I-2 | OCH$_3$ | 6-Cl | H | H | H |
| I-3 | OCH$_3$ | 5-F | H | H | H |
| I-4 | OCH$_3$ | 5-OCH$_3$ | H | H | H |
| I-5 | OCH$_3$ | 5-Cl | H | H | H |
| I-6 | OCH$_3$ | H | 2-F | H | H |
| I-7 | OCH$_3$ | H | 2-F | —COCH$_2$OCH$_3$ | H |
| I-8 | OCH$_3$ | H | 2-F | —COCH$_2$Cl | H |
| I-9 | OCH$_3$ | H | 3-F | —COCH$_2$Cl | H |
| I-10 | OCH$_3$ | 6-Cl | 4-F | H | H |
| I-11 | OCH$_3$ | H | 2-Cl | H | H |
| I-12 | OCH$_3$ | H | 2-Cl | —COCH$_2$Cl | H |
| I-13 | OCH$_3$ | H | 3-Cl | H | H |
| I-14 | OCH$_3$ | H | 3-Cl | —COCH$_2$Cl | H |
| I-15 | OCH$_3$ | H | 3-Cl | —COCH$_2$OCH$_3$ | H |
| I-16 | OCH$_3$ | H | 4-Cl | H | H |
| I-17 | OCH$_3$ | H | 4-Cl | —COCH$_2$Cl | H |
| I-18 | OCH$_3$ | H | 4-Cl | —COCH$_2$OCH$_3$ | H |
| I-19 | OCH$_3$ | 3-OCH$_3$ | 2-Br | H | H |
| I-20 | OCH$_3$ | H | 4-Br | H | H |
| I-21 | OCH$_3$ | H | 4-Br | —CO(CH$_2$)$_3$Cl | H |
| I-22 | OCH$_3$ | H | 4-Br | —CO(C$_6$H$_5$) | H |
| I-23 | OCH$_3$ | H | 4-Br | —COCHCl$_2$ | H |
| I-24 | OCH$_3$ | H | 4-Br | —COCH$_2$CH$_3$ | H |
| I-25 | OCH$_3$ | H | 4-Br | —COCHCl$_2$ | H |
| I-26 | OCH$_3$ | H | 2-I | H | H |
| I-27 | OCH$_3$ | H | 2-I | —COCH$_2$Cl | H |
| I-28 | OCH$_3$ | H | 3-I | H | H |
| I-29 | OCH$_3$ | H | 3-I | —COCH$_2$Cl | H |
| I-30 | OCH$_3$ | H | 3-I | —COCH$_2$OCH$_3$ | H |
| I-31 | OCH$_3$ | H | 4-I | H | H |
| I-32 | OCH$_3$ | H | 4-I | —COCH$_2$Cl | H |
| I-33 | OCH$_3$ | H | 4-I | —COCHCl$_2$ | H |
| I-34 | OCH$_3$ | H | 4-I | —COCH$_3$ | H |
| I-35 | OCH$_3$ | H | 4-I | —COCH$_2$OCH$_3$ | H |
| I-36 | OCH$_3$ | H | 2-CH$_3$ | H | H |
| I-37 | OCH$_3$ | H | 2-CH$_3$ | —COCH$_2$Cl | H |
| I-38 | OCH$_3$ | H | 4-CH$_3$ | H | H |
| I-39 | OCH$_3$ | H | 4-CH$_3$ | —COCH$_2$Cl | H |
| I-40 | OCH$_3$ | H | 2-CF$_3$ | H | H |
| I-41 | OCH$_3$ | H | 2-CF$_3$ | —COCH$_2$Cl | H |
| I-42 | OCH$_3$ | H | 4-CF$_3$ | H | H |
| I-43 | OCH$_3$ | H | 4-CF$_3$ | —COCH$_2$Cl | H |
| I-44 | OCH$_3$ | H | 4-OCH$_3$ | H | H |
| I-45 | OCH$_3$ | H | 4-OCH$_3$ | —COCHCl$_2$ | H |
| I-46 | OCH$_3$ | H | 4-OCH$_3$ | —CO(CH$_2$)$_3$Cl | H |
| I-47 | OCH$_3$ | H | 3,4-di-F | H | H |
| I-48 | OCH$_3$ | H | 2,5-di-Cl | H | H |
| I-49 | OCH$_3$ | H | 2,5-di-Cl | —COCH$_2$Cl | H |
| I-50 | OCH$_3$ | H | 2,3-di-Cl | H | H |
| I-51 | OCH$_3$ | H | 2,3-di-Cl | —COCH$_2$Cl | H |
| I-52 | OCH$_3$ | H | 3,4-di-Cl | H | H |
| I-53 | OCH$_3$ | H | 3,4-di-Cl | —COCH$_2$Cl | H |
| I-54 | OCH$_3$ | H | 3,4-di-Cl | —COCH$_2$OCH$_3$ | H |
| I-55 | OCH$_3$ | 3-OCH$_3$ | 3,4-di-Cl | H | H |
| I-56 | OCH$_3$ | H | 3,5-di-Cl | H | H |
| I-57 | OCH$_3$ | H | 3,5-di-Cl | —COCH$_2$Cl | H |
| I-58 | OCH$_3$ | H | 2,4-di-Cl | H | H |
| I-59 | OCH$_3$ | H | 2,4-di-Cl | —COCH$_2$Cl | H |
| I-60 | OCH$_3$ | H | 2,4-di-Cl-3-F | H | H |

TABLE 1-continued 2-pyrimidinyloxy-N-aryl-benzylamine derivatives

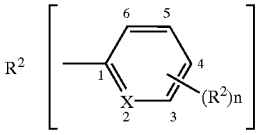

| Compound No. | D=E | R¹ | R² | R³ | X |
|---|---|---|---|---|---|
| I-61 | OCH₃ | 3-OCH₃ | 2,4-di-Cl-3-F | H | H |
| I-62 | OCH₃ | H | 2-F-4-Br | H | H |
| I-63 | OCH₃ | 3-OCH₃ | 2-F-4-Br | H | H |
| I-64 | OCH₃ | H | 2-CH₃-5-Cl | H | H |
| I-65 | OCH₃ | H | 2-CH₃-5-Cl | —COCH₂Cl | H |
| I-66 | OCH₃ | H | 2-CH₃-3-Cl | H | H |
| I-67 | OCH₃ | H | 2,4-di-CH₃ | H | H |
| I-68 | OCH₃ | H | 2,4-di-CH₃ | —COCH₂Cl | H |
| I-69 | OCH₃ | H | 3,4-di-CH₃ | H | H |
| I-70 | OCH₃ | H | 2,6-di-CH₂CH₃ | H | H |
| I-71 | OCH₃ | H | 3,4-di-CH₃ | —COCH₂Cl | H |
| I-72 | OCH₃ | H | 2,6-di-CH₂CH₃ | —COCH₂Cl | H |
| I-73 | OCH₃ | H | 2-Cl-5-CF₃ | H | H |
| I-74 | OCH₃ | H | 2-Cl-5-CF₃ | —COCH₂Cl | H |
| I-75 | OCH₃ | H | 4-NO₂ | H | H |
| I-76 | OCH₃ | H | 4-CO₂CH₃ | H | H |
| I-77 | OCH₃ | H | 4-CO₂CH₂CH₃ | H | H |
| I-78 | OCH₃ | H | 4-CO₂CH₂CH₂CH₃ | H | H |
| I-79 | OCH₃ | H | 4-CO₂CH(CH₃)₂ | H | H |
| I-80 | OCH₃ | H | 4-CO₂CH₂CH₂CH₂CH₃ | H | H |
| I-81 | OCH₃ | H | 4-CO₂C(CH₃)₃ | H | H |
| I-82 | OCH₃ | H | 4-CO₂CH₂CH(CH₃)₂ | H | H |
| I-83 | OCH₃ | H | 4-CO₂CH₂CF₃ | H | H |
| I-84 | OCH₃ | H | 4-CO₂CH₂CF₂CF₂H | H | H |
| I-85 | OCH₃ | H | 4-CO₂CH(CF₃)₂ | H | H |
| I-86 | OCH₃ | H | 4-CO₂CH₂C≡CH | H | H |
| I-87 | OCH₃ | H | 4-CO₂CH₂CH=CH₂ | H | H |
| I-88 | OCH₃ | 5-n-C₉H₁₉ | 4-CO₂CH₂CH₂CH₃ | H | H |
| I-89 | OCH₃ | 3-OCH₃ | 4-CO₂CH₂CH₂CH₃ | H | H |
| I-90 | OCH₃ | H | 2-CO₂CH₃ | H | H |
| I-91 | OCH₃ | H | 2-CO₂CH₂CH₃ | H | H |
| I-92 | OCH₃ | H | 2-CO₂CH₂CH₂CH₃ | H | H |
| I-93 | OCH₃ | H | 3-CO₂CH₃ | H | H |
| I-94 | OCH₃ | H | 3-CO₂CH₂CH₃ | H | H |
| I-95 | OCH₃ | H | 3-CO₂CH₂CH₂CH₃ | H | H |
| I-96 | OCH₃ | H | 3-CO₂CH(CH₃)₂ | H | H |
| I-97 | OCH₃ | H | 4-CON(CH₂CH₃)₂ | H | H |
| I-98 | OCH₃ | H | 4-CONHCH₂CH₃ | H | H |
| I-99 | OCH₃ | H | 4-CONHCH₂CH₂CH₃ | H | H |
| I-100 | OCH₃ | H | 4-CO₂H | H | H |
| I-101 | OCH₃ | H | 4-NHCOCH(CH₃)₂ | H | H |
| I-102 | OCH₃ | H | 4-NHCO(C₆H₅) | H | H |
| I-103 | OCH₃ | H | 4-NHCOCF₃ | H | H |
| I-104 | OCH₃ | H | 4-NHCOCH₃ | H | H |
| I-105 | OCH₃ | 3-OCH₃ | 4-NHCOCH(CH₃)₂ | H | H |
| I-106 | OCH₃ | 3-OCH₃ | 4-NHCOCH₃ | H | H |
| I-107 | OCH₃ | H | 4-NHCOCH(CH₃)₂ | Ac | H |
| I-108 | OCH₃ | H | 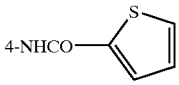 | H | H |
| I-109 | OCH₃ | H | 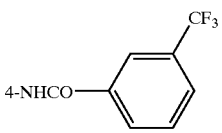 | H | H |
| I-110 | OCH₃ | H | 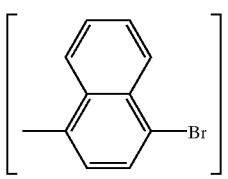 | H | H |

TABLE 1-continued
2-pyrimidinyloxy-N-aryl-benzylamine derivatives
| Compound No. | D=E | R¹ | | R³ | X |
|---|---|---|---|---|---|
| I-111 | OCH₃ | H | 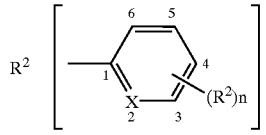 | H | H |
| I-112 | OCH₃ | H | 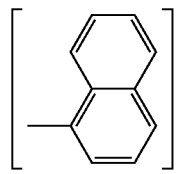 | —COCH₂Cl | H |
| I-113 | OCH₃ | H | 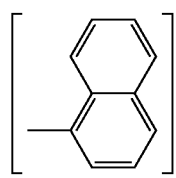 | H | H |
| I-114 | OCH₃ | H | 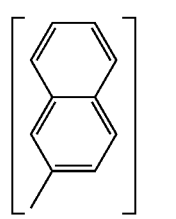 | —COCH₂Cl | H |
| I-115 | OCH₃ | H | H 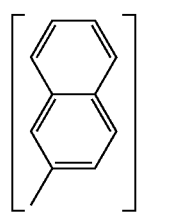 | H | N |
| I-116 | OCH₃ | 6-Cl | H 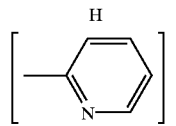 | H | N |
| I-117 | OCH₃ | H | 3-CH₃ 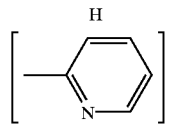 | H | N |
| I-118 | OCH₃ | H | 4-CH₃ 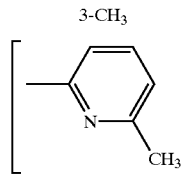 | H | N |

TABLE 1-continued 2-pyrimidinyloxy-N-aryl-benzylamine derivatives

| Compound No. | D=E | R¹ | [structure with (R²)n] | R³ | X |
|---|---|---|---|---|---|
| I-119 | OCH₃ | H | 5-CH₃, 2-methyl-4-methylpyridine | H | N |
| I-120 | OCH₃ | H | 5-CH₃, 2-methyl-4-methylpyridine | —COCHCl₂ | N |
| I-121 | OCH₃ | H | 5-CH₃, 2-methyl-4-methylpyridine | —COCH₂CH₃ | N |
| I-122 | OCH₃ | H | 4-Cl, 5-chloropyridin-2-yl | H | N |
| I-123 | OCH₃ | H | 6-(4,6-dimethoxy-2-pyrimidinyl)oxy, 2-methylpyridine structure | H | N |

2-pyrimidinyloxy-N-aryl-benzylamine derivatives according to the present invention can be synthesized by the following reaction scheme:

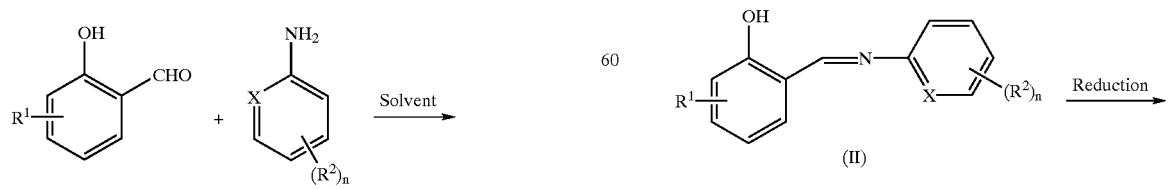

-continued

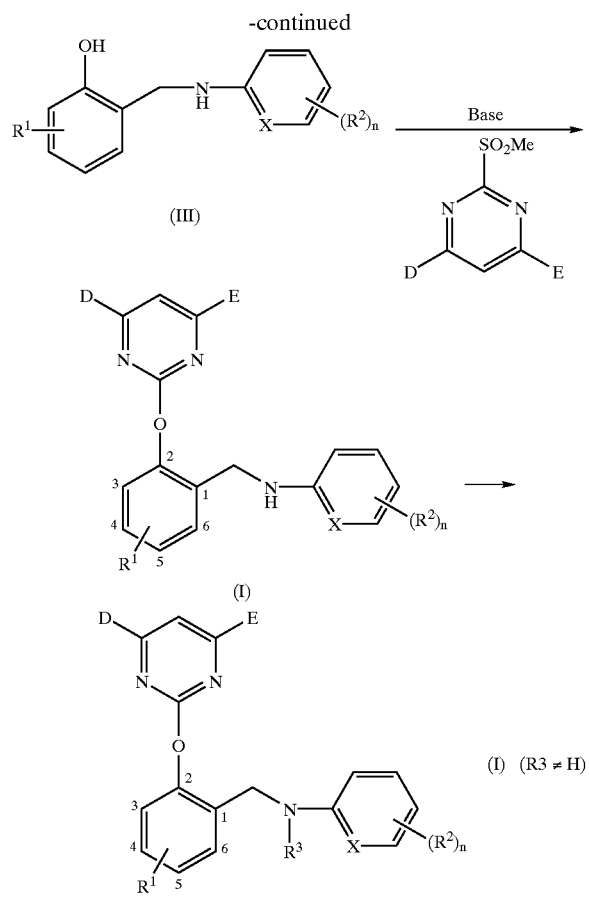

The substituents represented by $R^1$, $R^2$, $R^3$, D and E in the above reaction scheme are as described above. X is hydrogen or nitrogen atom.

The intermediate (II) was prepared by the reaction between salicylal and aromatic amine with molar ratio of 1:1 to 1:2. The solvent for the reaction can be a hydrocarbon solvent such as benzene, toluene or xylene and the like; a halogenated hydrocarbon solvent such as dichloromethane, dichloroethane or chloroform; an ether solvent such as tetrahydrofuran or dioxane; a ketone solvent such as acetone or methyl isobutyl ketone; an alcohol solvent such as methanol, ethanol or isopropanol; dimethylformamide; dimethylsulfoxide; acetonitrile; and the mixture thereof. The best solvent for the reaction is an alcohol solvent. The reaction temperature is in the range of room temperature to boiling point of the solvent used and the reaction time is 0.5 to 12 hours. The reaction can be conducted without a catalyst, although the addition of a catalyst can sometimes promote the speed and yield of the reaction. The catalyst used in the reaction can be p-methyl benzenesulfonic acid, methanesulfonic acid, sulfuric acid, hydrochloric acid or acetic acid and the like. The recommended molar ratio of catalyst to aromatic amine is (0.01–0.1):1.

The intermediate (III) can be prepared by reducing the compound (II). The reductant can be sodium borohydride or potassium borohydride. The molar ratio of the reactant (II) to reductant is 1:(0.5–2). The reaction temperature is in the range of room temperature to 40° C. and the reaction time is 0.5 to 10 hours. The solvent for the reaction can be a hydrocarbon solvent such as benzene, toluene or xylene; an ether solvent such as tetrahydrofuran or dioxane; an alcohol solvent such as methanol, ethanol or isopropanol; or dimethylformamide; dimethylsulfoxide; acetonitrile; and the mixture thereof. The best solvent for the reaction is an alcohol solvent. Furthermore, the intermediate (III) can also be obtained by reducing the compound (II) with hydrogen under the action of catalyst. The catalyst can be Raney nickle, palladium-carbon or platinum black and the like. The molar ratio of the reactant (II) to catalyst is 1:(0.01–0.5). The reaction temperature is in the range of room temperature to 40° C. and the reaction time is 0.5–10 hours. The solvent for the reaction can be a hydrocarbon solvent such as benzene, toluene or xylene; an ether solvent such as tetrahydrofuran or dioxane; an alcohol solvent such as methanol, ethanol or isopropanol; or dimethylformamide; dimethylsulfoxide; acetonitrile; and the mixture thereof. The best solvent for the reaction is an alcohol solvent.

Finally, the intermediate (III) is reacted with 2-methylsulfonyl-4D,6E-substituted pyrimidine in the present of a base to prepare the target product (I, $R^3$=H). In this reaction step, the base used can be a hydride, alkoxide compound or carbonate of monovalent or divalent metals, such as sodium hydride, potassium hydride, calcium hydride; sodium methoxide or sodium ethoxide, potassium methoxide or potassium ethoxide; sodium carbonate, potassium carbonate or calcium carbonate, or an organic base such as triethylamine, pyridine and the like. The reaction solvent can be a hydrocarbon solvent such as benzene, toluene or xylene; a halogenated hydrocarbon such as dichloromethane, dichloroethane or chloroform; an ether solvent such as tetrahydrofuran or dioxane; a ketone solvent such as acetone or methyl isobutyl ketone; an alcohol solvent such as methanol, ethanol or isopropanol; or dimethylformamide; dimethylsulfoxide; acetonitrile; and the mixture thereof. The best solvent for the reaction is an ether solvent. The reaction temperature is in the range of room temperature to the boiling point of the solvent used and the reaction time is 0.5–20 hours. The molar ratio of the intermediate (III) to 2-methylsulfonyl-4-D,6-E-substituted pyrimidine to the base is 1:(1.0–1.2):(1–5). The final product is purified by chromatography on silica gel column or recrystallization.

The target product 2-pyrimidinyloxy-N-aryl-benzylamine (I, $R^3$=H) can further react with appropriate acid anhydride or acid chloride to form the corresponding N-acylated product of 2-pyrimidinyloxy-N-aryl-benzylamine (I, $R^3 \neq H$).

As described previously, the resulting compound (3) represented by formula (I, R=H) is one of the active materials with weed control activity in the present invention. Moreover, if it is further reacted with an acid anhydride or an acid chloride $R^3$Cl in a solvent in the present of a base, N-acylated product as represented by formula (I) (R≠H) also having weed control activity can be obtained.

$R^3$ in the reaction scheme is $C_1$–$C_4$ alkoxyacetyl or haloacetyl, D and E, $R^1$–$R^3$ are as described above, $R^3$ in the reaction scheme is $C_1$–$C_4$ alkoxyacetyl or haloacetyl.

To a solvent in the present of a base and at a temperature from room temperature to the reflux temperature, was added the compound (3) represented by formula (I, R=H) and an acid anhydride or acid chloride $R^3$Cl and a base with a molar ratio of 1:(1.0–4):(0–2) and stirred for 2–8 hours to give the compound represented by formula (I) (R≠H) which also has weed control activity. The solvent and base used are the same as those in the third step during the synthesis of compound (3) as shown by formula (I) (R=H) described above. When the molar ratio of the compound (3) shown by the above 2-pyrimidinyloxy-N-aryl-benzylamine (I, $R^3$=H) represented by formula (I) (R=H) to the acid anhydride or acid chloride $R^3$Cl to the base was 1:(1.0–4):(0–2), the reaction was carried out for 2–8 hours in a solvent at a temperature from room temperature to the reflux temperature, to give a compound as shown in formula (I) (R≠H), the N-acylated product of 2-pyrimidinyloxy-N-aryl-benzylamine (I, R³≠H).

In order to use effectively, the compound of the present invention can be used as an active ingredient in herbicides. To the present compound, various additives such as water, organic solvents, surfactants, carriers can be added so as to formulate liquors, oil preparations, emulsions, powder preparations, granule preparations or capsule preparations which can be used in weed control for crops such as rape, cotton, paddy and soybean.

The compounds and the preparations thereof according to the present invention have the following characteristics and advantages:

1. They have relative high efficiency of weed control, and can exhibit good post-emergence weed control at a low dosage.
2. They have a broad spectrum of weed control, that is, they not only can prevent and weed out Gramineae weeds, but also can prevent and weed out broadleaf weeds and sedge, and they have an very effective weeding activity to aged Gramineae weeds (3–7 leaves).
3. They have high safety to crops such as rape, cotton, paddy, and soybean.
4. They have short residual life in soil, have no adverse effect to crops after crop rotation.
5. They have no evident toxicity to mammals or fish, and have relative high environmental safety. That is to say, they are low toxic and environmental friendly agricultural chemicals.

The compounds of formula (I) provided by the present invention and the preparations thereof can effectively prevent most of weeds in farmlands. They can effectively prevent Gramineae weeds in low dosage, and effectively prevent broadleaf weeds and Cyperus (sedge) in high dosage. The specific examples to be prevented and weeded include *Echinochloa crusgalli, Digitaria sanguinalis, Eleusine indica, Setaria viridis, Poa annua, Avena fatua, Alopecurus aequalis, Alopecurus japonicus, Amaranthus retroflexus, Amaranthus spinosus, Chenopodium album, Brassica juncea, Portulaca oleracea, Acalypha australis, Cyperus diffformis, Leptochloa chinensis, Cyperus rotundus, Fimbristylis miliacea, Stallaria media, Stellaria alsine, Erigeron annuus, Sagittaria sagittifolia, Convolvulus arvensis,* and the like.

The 2-pyrimidinyloxy-N-aryl-benzylamine derivatives of the present invention can be synthesized simply. The products have excellent weeding activity and are effective active substances for formulating herbicides in agriculture.

THE BEST EXAMPLES

Next, the detailed reaction conditions, purifying processes, physical constants and the analytical data required to determine structure are given with reference to some examples. However, it is noted that the present invention is not limited to the range of the following examples.

Example 1

The Synthesis of Compound No. I-78 in Table I 17.9 g (0.1 mol) of n-propyl 4-aminobenzoate is dissolved in 200 ml of anhydrous methanol. 14.6 g (0.12 mol) of salicylal is dropped into the solution. After stirred at room temperature for 50 min, the reaction mixture is filtered and the resulting solid is washed with anhydrous methanol to give 24.8 g of yellow solid n-propyl 4-(2-hydroxybenzylideneamino)benzamide. The intermediate is dissolved into 400 ml of anhydrous methanol and 3.8 g (0.10 mol) sodium borohydride is added into the solution in portions. After the mixture is stirred for 60 min, it is concentrated by removing methanol. 350 ml chloroform and 250 ml water are then added to the residue. The reaction mixture is well-stirred and then left to stand. The organic layer is separated and washed with saturated saline solution, dried over anhydrous sodium sulfate, and concentrated to give 22.7 g white solid n-propyl 4-(2-hydroxy-benzylamino) benzamide. The yield in the two steps is 80%.

The resulting intermediate n-propyl 4-(2-hydroxy-benzylamino) benzamide (22.7 g, 0.08 mol), 17.44 g (0.08 mol) of 2-methylsulfonyl-4,6-dimethoxypyrimidine are dissolved into 500 ml dioxane. 22 g (0.16 mol) of potassium carbonate is added at room temperature. The mixture is warm to reflux temperature for 11 hours, then suction filtered. The filter cake is washed with dioxane (50 ml×2) and the mother liquor is concentrated and recrystallized from ethyl acetate, giving 25.4 g of white solid product n-propyl 4-[2-(4,6-dimethoxy-2-pyrimidinyloxy)-benzylamino]-benzamide (I-78). The yield is 75%.

m.p.: 96–97° C.; m/z: 423 (M⁺); ¹HNMR (CDCl$_3$, δ): 7.14–7.88 (m, 8H), 6.51 (d, 1H), 5.78 (s, 1H), 4.45 (s, 2H), 4.19 (t, 2H), 3.80 (s, 6H), 1.77 (m, 2H), 1.03 (t, 3H) ppm Elemental analysis: C$_{23}$H$_{25}$N$_3$O$_5$ Calculated value C: 65.24; H: 5.95; N: 9.92. Found C: 65.52; H: 5.86; N: 9.83;

Example 2

The Synthesis of Compound No. I-79 in Table 1

17.9 g (0.1 mol) of i-propyl p-aminobenzoate is dissolved in 200 ml anhydrous methanol. 14.6 g (0.12 mol) of salicylal is dropped into the solution. After stirred at room temperature for 50 min, the reaction mixture is filtered and the resulting solid is washed with anhydrous methanol to give 24.8 g of yellow solid i-propyl 4-(2-hydroxybenzylideneamino)benzamide. The intermediate is dissolved into 400 ml anhydrous methanol and 3.8 g (0.10 mol) of sodium borohydride is added into the solution in portions. After the mixture is stirred to react for 60 min, it is concentrated by removing methanol. 350 ml chloroform and 250 ml water are then added to the residue. The mixture is well-stirred and then left to stand. The organic layer is separated and washed with saturated saline solution, dried over anhydrous sodium sulfate, and concentrated to give 23.3 g white solid i-propyl 4-(2-hydroxy-benzylamino) benzamide. The yield in the two steps is 82%.

The resulting intermediate i-propyl 4-(2-hydroxy-benzylamino)benzamide (23.3 g, 0.082 mol), 18.0 g (0.083 mol) of 2-methylsulfonyl-4,6-dimethoxypyrimidine are dissolved into 500 ml dioxane. 23 g (0.167 mol) of potassium carbonate is added at room temperature and the mixture is refluxed for 12 hours, then suction filtered. The filter cake is washed with dioxane (50 ml×2) and the mother liquor is concentrated and recrystallised from ethyl acetate, giving 27 g of white solid product i-propyl 4-[2-(4,6-dimethoxy-2-pyrimidinyloxy)-benzylamino]benzamide (I-79). The yield is 78%.

m.p.: 83–84° C.; m/z: 423 (M⁺); ¹HNMR (CDCl$_3$, δ): 7.11–7.86 (m, 6H), 6.52 (m, 2H), 5.77 (m, 1H), 5.22 (m, 1H), 4.43 (m, 2H), 3.80 (s, 6H), 3.70–3.90 (m, 1H), 1.35 (m, 6H) ppm. Elemental analysis: C$_{23}$H$_{25}$N$_3$O$_5$ Calculated value C: 65.24; H:5.95; N:9.92. Found C: 65.24; H: 5.95; N: 9.85.

The experimental steps for the following compounds are the same as that described in the example 1 and example 2. The analytical data is listed in the following table:

| Compound No. | Melting point m.p. | m/z | $^1$HNMR($\delta$, ppm) | Elemental analysis Calcd. | Elemental analysis Found |
|---|---|---|---|---|---|
| I-1 | 81.0 ± 0.5° C. | 337 | 3.81(s, 6H), 4.35(s, 2H), 5.78(d, 1H), 6.56(q, 2H), 6.59–6.72(t, 1H), 7.10–7.28(m, 4H), 7.28–7.46(q, 2H), 7.48 (d, 1H) | C: 67.66 H: 5.64 N: 12.46 | C: 67.82 H: 5.78 N: 12.74 |
| I-3 | 84.4 ± 0.5° C. | 355 | 3.78(s, 6H), 4.52(s, 2H), 4.96(d, 1H), 5.75(d, 1H), 7.01(m, 8H) | C: 64.23 H: 5.07 N: 11.83 | C: 64.42 H: 4.98 N: 11.85 |
| I-4 | 96.6 ± 0.5° C. | 367 | 3.77(s, 3H), 3.81(s, 6H), 4.30(s, 2H), 5.77(s, 1H), 6.59–6.83(m, 3H), 7.03–7.15(m, 5H) | C: 65.40 H: 5.76 N: 11.44 | C: 65.50 H: 5.72 N: 11.33 |
| I-5 | 93.5 ± 0.5° C. | 371 | 3.77(s, 6H),4.31(s, 2H), 5.79(d, 1H), 6.59(d, 2H), 6.72(t, 1H), 7.10–7.27(m, 5H) | C: 61.38 H: 4.88 N: 11.30 | C: 61.38 H: 4.92 N: 11.23 |
| I-6 | 104.0 ± 0.3° C. | 355 | 3.71(6H), 4.37(2H), 5.76(1H), 6.60–7.46(8H) | | |
| I-11 | 94.1 ± 0.3° C. | 371 | 3.78(6H), 4.36(1H), 4.40(2H), 5.76 (1H), 6.60–7.34(8H) | | |
| I-13 | 108.2 ± 0.3° C. | 371 | 3.80(6H), 4.19(1H), 4.30(2H), 5.77 (1H), 6.38–7.40(8H) | | |
| I-16 | 114.1 ± 0.3° C. | 371 | 3.79(6H), 4.29(2H), 5.71(1H), 6.25–7.38(8H) | | |
| I-19 | 176.2 ± 0.5° C. | 446 | 2.84(s, 3H), 3.76(s, 6H), 4.43(d, 2H), 5.24(s, 1H), 5.81(s, 1H), 6.48–6.54(t, 1H), 6.62(d, 1H), 7.01–7.10(m, 3H), 7.19(t, 1H) | C: 53.83 H: 4.52 N: 9.42 Br: 17.90 | C: 54.32 H: 4.18 N: 9.43 Br: 17.80 |
| I-20 | — | 417 | 3.81(s, 6H), 4.33(s, 2H), 5.78(s, 1H), 6.45(d, 1H), 7.11–7.48(m,8H) | | |
| I-26 | 110.6 ± 0.3° C. | 463 | 3.79(6H), 4.40(2H), 4.50(1H), 5.77 (1H), 6.38–7.63(8H) | | |
| I-28 | 113.0 ± 0.3° C. | 463 | 3.79(6H), 4.18(1H), 4.28(2H), 5.77 (1H), 6.44–7.41(8H) | | |
| I-31 | — | 463 | 3.80(s, 6H), 4.32(s, 2H), 5.78(s, 1H), 6.37(d, 1H), 7.13–7.50(m,8H) | | |
| I-36 | 95.3 ± 0.3° C. | 351 | 2.07(3H), 3.79(6H), 4.05(1H), 4.38 (2H), 5.76(1H),5.53–7.45(8H) | | |
| I-38 | 75.6 ± 0.3° C. | 351 | 2.20(3H), 3.80(6H), 4.29(2H), 5.76 (1H), 6.25–7.46(8H) | | |
| I-40 | 97.7 ± 0.3° C. | 405 | 3.79(6H), 4.41(2H), 4.78(1H), 5.77 (1H), 6.63–7.42(8H) | | |
| I-42 | 116.9 ± 0.3° C. | 405 | 3.78(6H), 4.37(2H), 4.42(1H), 5.77 (1H), 6.50–7.41(8H) | | |
| I-44 | — | 366 | 3.77(s, 3H), 4.30(s, 2H), 4.83(s, 6H), 5.78(s, 1H), 6.53(d, 1H), 6.72(d, 2H), 7.06–7.48 (m, 6H) | | |
| I-47 | 131.6 ± 0.3° C. | 373 | 3.85(s, 6H), 4.32(m, 2H), 5.82(s, 1H), 6.13–6.39(m, 2H), 6.90(m, 1H), 7.2–7.51(m, 4H) | C: 61.12 H: 4.59 N: 11.25 | C: 61.13 H: 4.61 N: 11.25 |
| I-48 | 115.3 ± 0.3° C. | 405 | 3.85(6H), 4.50(2H), 5.85(1H), 6.40–7.70(7H) | | |
| I-50 | 116.7 ± 0.3° C. | 405 | 3.78(6H), 4.41(2H), 4.85(1H), 5.77 (1H), 6.25–7.38(7H) | | |
| I-52 | 162.4 ± 0.3° C. | 405 | 3.79(6H), 4.20(1H), 4.28(2H), 5.77 (1H), 6.33–7.37(7H) | | |
| I-55 | 128.5 | 435 | 1.96(s, 1H), 2.82(s, 3H), | C: 55.06 | C: 55.03 |

-continued

| Compound No. | Melting point m.p. | m/z | ¹HNMR(δ, ppm) | Elemental analysis Calcd. | Elemental analysis Found |
|---|---|---|---|---|---|
| | ± 0.5 °C. | | 3.76(s, 6H), 4.32(s, 2H), 5.81(d, 1H), 6.55 (q, 1H), 6.70(d, 1H), 7.04(t, 2H), 7.14–7.18 (m, 2H) | H: 4.39 N: 9.36 Cl: 16.25 | H: 4.41 N: 9.42 Cl: 16.19 |
| I-56 | 146.6 ± 0.3 °C. | 405 | 3.80(6H), 4.29(2H), 5.78(1H), 6.36–7.37(7H) | | |
| I-58 | 77.6 ± 0.3° C. | 405 | 3.78(6H), 4.38(2H), 4.69(1H), 5.76 (1H), 6.49–7.39(7H) | | |
| I-60 | 101.2 ± 0.5 °C. | 423 | 3.78(s, 6H), 4.48 (d, 2H), 5.81(s, 1H), 5.84(s, 1H), 6.45–6.49(q, 1H),7.12–7.27(m, 3H), 7.36(t, 1H), 7.44 (d, 1H) | C: 53.79 H: 3.80 N: 9.90 Cl: 16.71 | C: 53.91 H: 3.94 N: 9.98 Cl: 16.54 |
| I-61 | 128.6 ± 0.5 °C. | 453 | 2.84(s, 3H), 3.76(s, 6H), 4.47(d, 2H), 5.73(s,1H), 5.81(s, 1H), 6.49(q,1H), 6.99–7.22(m, 4H) | C: 52.88 H: 3.99 N: 9.25 Cl: 15.61 | C: 52.93 H: 4.07 N: 9.37 Cl: 15.65 |
| I-62 | 63.5 ± 0.5° C. | 434 | 3.78(s, 6H), 4.40(d,2H), 5.51(s, 1H), 5.84(s,1H), 6.54–6.60(t, 1H), 7.01–7.05(d, 1H), 7.13–7.25(m, 3H), 7.32–7.38(t, 1H),7.46–7.48(d,1H) | C: 52.55 H: 3.95 N: 9.68 Br: 18.12 | C: 52.65 H: 4.02 N: 9.74 Br: 18.12 |
| I-63 | 146.9 ± 0.5 °C. | 464 | 2.83(s, 3H), 3.76(s,6H), 4.38–4.40 (d,2H), 5.46(s, 1H), 5.81(s, 1H), 6.55–6.61(t, 1H),7.01–7.05(m, 3H), 7.11–7.21(m, 2H) | C: 51.74 H: 4.13 N: 9.05 Br: 17.12 | C: 51.65 H: 3.75 N: 9.17 Br: 16.97 |
| I-64 | 116.5 ± 0.3 °C. | 385 | 3.00(3H), 3.85(6H), 4.40(2H), 5.80 (1H), 6.50–7.60(7H) | | |
| I-66 | 125.0 ± 0.3 °C. | 385 | 2.13(3H), 3.80(6H), 4.10(1H), 4.37 (2H), 5.77(1H), 6.44–7.42(7H) | | |
| I-67 | 163.7 ± 0.3 °C. | 365 | 2.06(3H), 2.20(3H), 3.80(6H), 4.35 (2H), 5.76(1H),6.44–7.45(7H) | | |
| I-69 | 91.4 ± 0.3° C. | 365 | 2.11(3H), 2.13(3H), 3.79(6H), 4.29 (2H), 5.76(1H),6.30–7.46(7H) | | |
| I-73 | 101.8 ± 0.3 °C. | 439 | 3.76(6H), 4.44(2H), 4.82(1H), 5.75 (1H), 6.79–7.42(7H) | | |
| I-75 | 173.2 ± 0.3 °C. | 382 | 3.79(s, 6H), 4.42(m, 2H), 5.78(m, 1H), 6.47(m, 2H), 7.39–7.16(m, 4H), 8.01 (d, 2H) | C: 59.68 H: 4.74 N: 14.65 | C: 59.82 H: 4.76 N: 14.89 |
| I-76 | 122.6 ± 0.5 °C. | 395 | 3.82(s, 9H), 4.40(m, 2H), 5.76(m, 1H), 6.50(m, 2H), 7.10–7.85 (m, 6H) | C: 63.79 H: 5.35 N: 10.63 | C: 63.80 H: 5.36 N: 10.48 |
| I-77 | 106.2 ± 0.5 °C. | 409 | 1.30(m, 3H), 3.28(m, 1H), 3.82(s, 6H), 4.26(m, 2H), 4.40(m, 2H), 5.85 (m, 1H), 6.65(m, 2H), 7.12–7.78(m, 6H) | C: 64.54 H: 5.66 N: 10.26 | C: 64.64 H: 5.72 N: 10.26 |
| I-80 | 121.1 ± 0.3 °C. | 437 | 0.95(m, 3H), 1.45(m, 2H), 1.73(m,2H), 3.84(s, 6H), 4.25(m,2H), 4.45 (m, 2H), 4.60(m,1H), 5.78(m, 1H), 6.50(m,2H), 7.11–7.90(m, 6H) | C: 65.89 H: 6.22 N: 9.60 | C: 66.20 H: 6.16 N: 9.48 |
| I-81 | 158.5 ± 0.5 °C. | 437 | 1.56(s,9H), 3.80(s, 6H), 4.38(m, 2H), 5.78(m, 1H), 6.50(m, 2H), 7.10–7.80 (m, 6H) | C: 65.89 H: 6.18 N: 9.61 | C: 65.95 H: 6.21 N: 9.60 |
| I-82 | 101.1 ± 0.3 °C. | 437 | 1.0(s, 6H), 2.05(m, 1H), 3.82(s, 6H), 4.02(m, 2H), 4.42(m, 2H), 4.66(m, 1H), 5.80(m, 1H), 6.53(m, 2H), 7.11–7.89(m, 6H) | C: 65.89 H: 6.22 N: 9.60 | C: 65.71 H: 6.27 N: 9.36 |
| I-83 | 132.9 ± 0.3 °C. | 463 | 3.83(s, 6H), 4.40(m, 2H), 4.58(m, 2H), 4.65(m, 1H), 5.77(m, 1H), 6.52(m, 2H), | C: 57.02 H: 4.35 N: 9.07 | C: 56.99 H: 4.45 N: 8.99 |

-continued

| Compound No. | Melting point m.p. | m/z | $^1$HNMR($\delta$, ppm) | Elemental analysis Calcd. | Elemental analysis Found |
|---|---|---|---|---|---|
| | | | 7.12–7.89(m, 6H) | | |
| I-84 | 137.8 ± 0.5 °C. | 495 | 3.28(m, 1H), 3.84(s, 6H), 4.45(m, 2H), 4.75(m, 2H), 5.85(m, 1H), 6.67 (m, 2H), 7.12–7.82(m, 6H) | C: 55.76 H: 4.27 N: 8.48 | C: 55.86 H: 4.37 N: 8.52 |
| I-85 | 127.4 ± 0.5 °C. | 531 | 3.26(m, 1H), 3.82(s, 6H), 4.46(m, 2H), 5.85(m, 1H), 6.46(m, 1H), 6.68–6.78 (m, 2H), 7.17–7.88(m, 6H) | C: 51.98 H: 3.60 N: 7.91 | C: 52.04 H: 3.75 N: 7.92 |
| I-86 | 112.3 ± 0.3 °C. | 419 | 2.48(m, 1H), 3.84(s, 6H), 4.40(m, 2H), 4.85(m, 2H), 5.77(m, 1H), 6.50 (m, 2H), 7.12–7.83(m, 6H) | | |
| I-87 | 96.5 ± 0.3° C. | 421 | 3.80(s, 6H), 4.39(m, 2H), 4.76(m, 2H), 5.40–5.22(m, 2H), 5.78(d, 1H), 6.01(d, 1H), 6.51(q, 2H), 7.84–7.14(m, 6H) | | |
| I-88 | Oil | 548 | 3.70(s, 6H), 4.17(s, 2H), 4.53(s, 2H), 5.75(d, 1H), 6.44(d, 2H), 7.34–7.02(m, 3H), 7.80–7.76(m, 2H) | C: 69.92 H: 7.88 N: 7.644 | C: 68.29 H: 7.86 N: 6.17 |
| I-89 | — | 453 | 6.92–7.48(m, 7H,), 6.34(m, 1H), 5.80 (m, 1H), 4.50(m, 2H), 4.28(m, 2H), 3.82(s, 9H), 1.75(m, 2H), 1.03(m, 3H) | | |
| I-90 | 67.1 ± 0.3° C. | 395 | 3.95(s, 9H) 4.52(s, 2H), 5.78(s, 1H), 6.65(m, 2H), 7.10–7.95(m, 6H) | | |
| I-91 | 74.5 ± 0.3° C. | 409 | 1.42(s, 3H), 3.80(s, 6H), 4.50(m, 2H), 5.75(m, 1H), 6.58(m, 2H), 7.18–7.95 (m, 6H) | | |
| I-92 | 58.6 ± 0.3° C. | 423 | 1.05(m, 3H), 1.75(m, 3H), 3.78(s, 6H), 4.15(m, 2H), 4.45(m, 2H), 5.75(m, 1H), 6.55(m, 2H), 7.15–7.90(m, 6H), 8.15(m, 1H) | | |
| I-93 | 136.3 ± 0.3 °C. | 395 | 3.79(s, 6H), 3.87(m, 3H), 4.40(m, 2H), 5.75(m, 1H), 6.70(m, 1H), 7.11–7.50 (m, 7H) | | |
| I-94 | 134.7 ± 0.3 °C. | 409 | 1.46(s, 3H), 3.90(s, 6H), 4.40(m,4H), 5.80(m, 1H), 6.67(m, 1H), 7.12–7.52 (m, 7H) | | |
| I-95 | 107.1 ± 0.3 °C. | 423 | 1.03(m, 3H), 1.76(m, 2H), 3.80(s, 6H), 4.25(m, 2H), 4.40(m, 2H), 5.75(m, 1H), 6.75(m, 1H), 7.10–7.55(m, 7H) | | |
| I-96 | 78.3 ± 0.3° C. | 423 | 1.30(s, 6H), 3.80(s, 6H), 4.36(m, 2H), 5.20(m, 1H), 5.77(m, 1H), 6.70(m, 1H), 7.08–7.50(m, 7H) | C: 65.24 H: 5.95 N: 9 92 | C: 64.85 H: 5.95 N: 9.87 |
| I-97 | 112.6 ± 0.3 °C. | 436 | 1.20(s, 6H), 3.45(m, 4H), 3.80(s, 6H), 4.35(m, 2H), 5.74(m, 1H), 6.54 (m, 2H), 7.15–7.49(m, 6H) | C: 66.04 H: 6.47 N: 12.84 | C: 65.97 H: 6.36 N: 12.65 |
| I-98 | 122.0 ± 0.3 °C. | 422 | 0.98(s, 3H), 1.57(m, 2H), 3.36(m, 2H), 3.81(s, 6H,), 4.38(m, 2H), 5.77 (m, 1H), 6.00(m, 1H), 6.52(m, 2H), 7.10–7.60(m, 6H) | C: 65.39 H: 6.20 N: 13.26 | C: 65.50 H: 6.24 N: 13.37 |
| I-99 | 130.6 ± 0.3 °C. | 436 | 0.95(m, 3H), 1.40(m, 2H), 1.55(m, 2H), 3.40(m, 2H), 3.78(s, 6H), 4.38 (m, 2H), 5.77(m, 1H), 5.98(m, 1H), 6.52(m, 2H,), 7.10–7.60(m, 6H) | C: 66.04 H: 6.47 N: 12.84 | C: 66.15 H: 6.38 N: 12.82 |
| I-100 | 168.1 ± 0.3 °C. | 381 | 1.10(m, 1H), 3.78(s, 6H), 4.27(m, 2H), 5.96(m, 1H), 6.54(m, 2H), 7.12–7.72 (m, 6H) | C: 63.00 H: 5.02 N: 11.02 | C: 62.23 H: 5.44 N: 10.22 |

-continued

| Compound No. | Melting point m.p. | m/z | $^1$HNMR($\delta$, ppm) | Elemental analysis Calcd. | Elemental analysis Found |
|---|---|---|---|---|---|
| I-101 | 134.4 ± 0.3 °C. | 422 | 1.24(d, 6H), 1.76(m, 1H), 2.45(m, 1H), 3.80(s, 6H), 4.35(m, 1H), 5.75 (m, 1H), 6.45–6.57(m, 2H), 6.96–7.49(m, 8H) | C: 65.39 H: 6.20 N: 13.26 | C: 65.39 H: 6.06 N: 13.40 |
| I-102 | 153.1 ± 0.3 °C. | 456 | 1.69(m, 1H), 3.82(s, 6H), 4.4(m, 1H), 5.75(m, 1H), 6.55(m, 2H), 7.1–7.9(m, 13H) | C: 68.41 H: 5.30 N: 12.27 | C: 67.70 H: 5.34 N: 12.12 |
| I-103 | 159.3 ± 0.3 °C. | 448 | 1.6(m, 1H), 3.84(s, 6H), 4.36(m, 1H), 5.78(m,1H), 6.56(m,2H), 7.10–7.78(m, 8H) | C: 56.25 H: 4.27 N: 12.49 | C: 56.37 H: 4.27 N: 12.54 |
| I-104 | 162.4 ± 0.3 °C. | 394 | 1.70(m, 1H), 2.12(s, 3H), 3.80(s, 6H), 4.25(s, 1H), 5.80(m, 1H), 6.5 (m, 2H), 7.10–7.5(m, 8H) | C: 63.95 H: 5.62 N: 14.20 | C: 64.49 H: 5.78 N: 13.80 |
| I-105 | 171.9 ± 0.5 °C. | 452 | 0.87(d, 6H), 2.22–2.32(m, 1H), 2.59(s, 3H), 3.53(s, 6H), 4.02–4.03(d, 2H), 4.97(S, 1H), 5.57(s, 1H), 6.27(d, 2H), 6.75–6.82(m, 2H), 6.88–6.93(t, 1H), 7.08–7.11(d, 2H), 8.40 (s, 1H) | C: 63.70 H: 6.24 N: 12.38 | C: 63.79 H: 6.55 N: 12.41 |
| I-106 | 170.2 ± 0.5 °C. | 424 | 1.72(s, 1H), 2.59(s, 3H), 3.52(s, 6H), 4.01–4.03(d, 2H), 4.97(s, 1H), 5.56(s, 1H), 6.27(d,2 H), 6.74–6.82(m, 2H), 6.88–6.93(t, 1H), 7.05(d, 2H), 8.50(s, 1H) | C: 62.25 H: 5.70 N: 13.20 | C: 61.86 H: 5.71 N: 13.10 |
| I-108 | 147.5 ± 0.3 °C. | 464 | 1.76(m, 1H), 3.84(s, 6H), 4.16(m, 1H), 4.35(m, 2H), 5.76(m, 1H), 6.52 (m, 2H), 7.0–7.78(m, 8H) | C: 62.32 H: 4.79 N: 12.11 | C: 62.21 H: 4.73 N: 12.13 |
| I-109 | 150.4 ± 0.3 °C. | 524 | 1.65(m, 1H), 3.82(s, 6H), 4.30(m, 1H), 5.8(m, 1H), 6.55(m, 2H), 7.1–8.15(m, 12H) | C: 61.83 H: 4.42 N: 10.68 | C: 61.85 H: 4.46 N: 10.67 |
| I-110 | — | 465 | 3.79(s, 6H), 4.53(s, 2H), 5.61(s, 1H), 6.48 (d, 1H), 7.13–8.19 (m, 10H) | | |
| I-111 | 124.1 ± 0.3 °C. | 387 | 3.70(6H), 4.35(1H), 4.50(2H), 5.60 (1H), 6.40–7.90(11H) | | |
| I-113 | 126.2 ± 0.3 °C. | 387 | 3.70(6H), 4.35(1H), 4.50(2H), 5.60 (1H), 6.40–7.90(11H) | | |
| I-115 | 94.0 ± 0.3° C. | 338 | 3.81(6H), 4.50(2H), 5.28(1H), 6.30–7.50(7H), 8.25(1H) | | |
| I-117 | 101.4 ± 0.3 °C. | 352 | 2.50(3H), 3.85(6H), 4.50(2H), 5.20 (1H), 5.85(1H),6.10–7.70(7H) | | |
| I-118 | 79.8 ± 0.3° C. | 352 | 2.10(3H), 3.85(6H), 4.50(2H), 5.00 (1H), 5.75(1H),6.20–7.90(7H) | | |
| I-119 | 90.4 ± 0.3° C. | 352 | 2.14(s, 3H), 3.81(s, 6H), 4.50(d, H), 5.00(s, 1H), 5.78(s, 1H), 6.12(s, H), 6.39(d, 1H), 7.10–7.93 (m, 5H) | | |
| I-122 | 103.9 ± 0.3 °C. | 372 | 3.80(6H), 4.50(2H), 5.10(1H), 5.80 (1H), 6.20–7.50(6H),8.05(1H) | | |
| I-123 | 115.5 ± 0.3 °C. | 352 | 1.95(3H), 3.75(6H), 4.60(1H), 4.72 (2H), 5.75(1H), 6.35–7.70 (6H), 8.10(1H) | | |

Example 3

The Synthesis of Compound No. I-107 in Table 1

1.38 g (10 mmol) p-nitroaniline is dissolved in 10 ml of glacial acetic acid and 1.88 ml (20 mmol) acetic anhydride is slowly dropped into the solution. The mixture is heated to reflux temperature for 30 min, cooled to room temperature and added into ice water. It is filtered, washed to neutral with ice water, dried, to give 1.688 g of product. The yield is 93.8%.

1.688 g (9.38 mmol) p-acetamino nitrobenzene is dissolved in 10 ml of anhydrous methanol. Suitable amount, i.e., 0.1266 g Raney-Ni and 0.83 g (14.1 mmol, 85%) hydrazine hydrate is added to the solution. The mixture is reacted for 6 hours, and then suction filtered. The filtrate is concentrated to give a product, p-acetamino aniline. The yield reaches the theoretical value.

1.405 g (9.37 mmol) p-acetamino aniline is dissolved in 15 ml anhydrous ethanol. 1.709 g (11.44 mmol) of o-vanillin is added and reacted completely at room temperature with stirring. TLC is used to control the end point of the reaction. The reaction mixture is filtered. The resulting solid is washed with anhydrous ethanol, to give 2.177 g of yellow solid product. The yield is 81.8%.

2.177 g (7.665 mmol) of the resulting compound is dissolved in 20 ml anhydrous ethanol. 0.445 g (11.5 mmol, 96%) sodium borohydride is added in portions and stirred for 30 minutes at room temperature. The reactants are poured into ice water, filtered, dried, to give 2.190 g of product. The yield reached the theoretical value.

2.190 g (7.66 mmol) of the resulting compound above, 1.670 g (7.66 mmol) of 2-methylsulfonyl-4,6-dimethoxypyrimidine are dissolved into 30 ml of dioxane. 2.114 g (15.32 mmol) potassium carbonate is added at room temperature. The mixture is refluxed to react for 11 hours, and then suction filtered. The filter cake is washed with 20 ml dioxane and the mother liquor is concentrated. The residual product is added into 10 ml of ethanol while stirring, then suction filtered, to give 2.83 g of white solid product, N-{4-[2-(4,6-dimethoxy-2-pyrimidinyloxy)-3-methoxybenzyl amino]phenyl}acetamide. The yield is 87.0%. The product is purified by recrystallization from ethyl acetate.

0.604 g (1.533 mmol) of N-{4-[2-(4,6-dimethoxy-2-pyrimidinyloxy)-3-methoxybenzyl amino]phenyl}acetamide and 0.423 g (3.066 mmol) of potassium carbonate are dissolved in 10 ml of anhydrous tetrahydrofuran. 0.13 ml (1.84 mmol) of acetyl chloride is dropped and the reaction temperature is controlled below 20° C. The reaction mixture is stirred at room temperate till the completion of reaction and filtered. The solvent is removed under the reduced pressure to give 0.654 g of N-acetamino-N-{4-[2-(4,6-dimethoxy-2-pyrimidinyloxy)-3-methoxybenzylamino]phenyl}acetamide which is purified by column chromatography (ethyl acetate/n-hexane). The yield is 97.8%.

The experimental steps of the following compounds are the same as that of Example 3. The data is listed in the following table:

| Compound No. | Melting point m.p. | m/z | $^1$HNMR($\delta$, ppm) | Elemental analysis Calcd. | Elemental analysis Found |
|---|---|---|---|---|---|
| I-18 | 145.5 ± 0.3° C. | 443 | 3.30(3H), 3.73(2H), 3.76(6H), 4.96(2H), 5.73(1H), 6.92–7.46 (8H) | | |
| I-21 | 139.1 ± 0.3° C. | 521 | 2.01(m, 2H), 2.20(t, 2H), 3.52 (t, 2H), 3.79(s, 6H), 4.99(s, 2H), 5.76(s, 1H), 6.82(m, 8H) | | |
| I-22 | 122.3 ± 0.3° C. | 520 | 3.76(s, 6H), 5.20(s, 2H), 5.75 (s, 1H), 6.74–7.61 (m, 13H) | | |
| I-23 | 137.2 ± 0.3° C. | 527 | 3.85(s, 6H), 5.03(s, 2H), 5.79(s, 1H), 5.81(s, 1H), 6.92–7.48(m, 8H) | | |
| I-24 | 109.0 ± 0.3° C. | 473 | 1.03(t, 3H), 2.09(q, 2H), 3.81(s, 6H), 4.99(s, 2H), 5.76(s, 1H), 6.82–7.51 (m, 8H) | | |
| I-25 | — | 492 | 3.79(s, 6H), 3.81(s, 2H), 4.99(s, 2H), 5.76(s, 1H), 6.90–7.48(m, 8H) | | |
| I-35 | 137.0 ± 0.3° C. | 535 | 3.33(3H), 3.74(2H), 3.77(6H), 4.97(2H), 5.76(1H), 6.73–7.52 (8H) | | |
| I-45 | 137.0 ± 0.3° C. | 477 | 3.79(s, 9H), 4.99(s, 2H), 5.70(s, 1H), 5.82(s, 1H), 6.58–7.44 (m, 8H) | | |
| I-46 | 107.0 ± 0.3° C. | 471 | 2.05(m, 2H), 2.22(t, 2H), 3.50 (t, 2H), 3.79(s, 9H), 4.99(s, 2H), 5.72 (s, 1H), 6.56–7.44 (m, 8H) | | |
| I-49 | 121.5 ± 0.3° C. | 481 | 2.03(3H), 3.68(2H), 3.77(6H), 4.70(1H), 5.27(1H), 5.71(1H), 6.88–7.54(7H) | | |

-continued

| Compound No. | Melting point m.p. | m/z | $^1$HNMR($\delta$, ppm) | Elemental analysis Calcd. | Elemental analysis Found |
|---|---|---|---|---|---|
| I-57 | 101.6 ± 0.3° C. | 481 | 3.76(6H), 3.81(2H), 5.00(2H), 5.75(1H), 6.98–7.40(7H) | | |
| I-59 | 132.2 ± 0.3° C. | 481 | 3.69(1H), 3.76(6H), 3.79(1H), 4.46(1H), 5.47(1H), 5.74(1H) 6.94–7.48(7H) | | |
| I-65 | 116.5 ± 0.3° C. | 461 | 3.73(1H), 3.79(6H), 3.80(1H), 4.58(1H), 5.40(1H), 5.73(1H), 7.06–7.48(7H) | | |
| I-68 | 113.9 ± 0.3° C. | 441 | 1.92(6H) 3.65(2H), 3.75(6H) 4.99(2H), 5.64(1H), 6.80–7.73 (7H) | | |
| I-72 | 101.8 ± 0.3° C. | 469 | 0.98(6H), 2.30(4H), 3.76(6H), 4.96(2H), 6.66(1H), 6.93–7.67 (7H) | | |
| I-74 | 94.7 ± 0.3° C. | 515 | 3.65(1H), 3.75(6H), 3.80(1H), 4.52(1H), 5.44(1H), 5.72(1H), 7.09–7.52(7H) | | |
| I-107 | 152.4 ± 0.5° C. | 436 | 1.79(s, 1H), 2.83(s, 3H), 3.71(s, 6H), 4.90(s, 2H), 5.74(s, 1H), 7.05–7.12(t, 3H), 7.21–7.30(m, 2H), 7.47–7.55(q, 3H), 9.20(s, 1H) | C: 63.29 H: 5.54 N: 12.84 | C: 63.41 H: 5.61; N: 13.00 |
| I-112 | 115.1 ± 0.3° C. | 463 | 3.62(6H), 3.63(1H), 3.66(1H), 4.65(1H), 5.58(1H), 5.65(1H), 7.10–7.80(11H) | | |
| I-120 | Oil | 471 | 2.32(s, 3H), 3.81(s, 6H), 5.18(s, 2H), 5.75(s, 1H), 6.59(s, 1H), 7.00–8.30 (m, 7H) | | |
| I-121 | 69.7 ± 0.3° C. | 408 | 1.11(t, 3H), 2.35(m, 5H), 3.78 (s, 6H), 5.12(s, 2H), 5.75(s, 1H), 6.88–8.26 (m, 7H) | | |

Example 4

Wettable Powder Preparations

Next, the specific examples of formulating several herbicide dosage forms are given, in which the compounds (take compound I-78 as example) of the present invention are used as active ingredients. It is noted that the present invention is not limited in the range of the following examples. In these examples of formulations, all "%" is refer to weight percent, "g ai/ha" is refer to one gram active material per hectare.

15% of compound (I-78) (Table 1), 5% of ligninsulfonate (M$_g$), 1% of lauryl alcohol polyoxyethylene ether (JFC), 40% of diatomite and 44% of light weight calcium carbonate are uniformly mixed and comminuted to give a wettable powder preparations.

Example 5

Emulsion

10% of compound (I-78) (Table 1), 5% of Agricultural Emulsion No. 500 (calcium salt), 5% of Agricultural Emulsion No. 602, 5% of N-methyl-2-pyrrolidone and 75% of xylene are heated while stirring, to give the emulsion.

Example 6

Granule Preparations

5% of compound (I-78) (Table 1), 1% of polyvinyl alcohol(PVA), 4% of sodium naphthalene sulfonate-formaldehyde condensate (NMO) and 90% of clay are uniformly mixed and comminuted. Then, 20 parts of water is added to 100 parts of the mixture. The mixture is kneaded and prepared into the granules with the size of 14-32 mesh, then dried, to give the granule preparations.

Example 7

The Method for Biological Testing Activity

Next, the examples for conducting the test of biological activity on the compounds of the present invention are given. It is noted that the present invention is not limited in the range of the following examples.

The 5-grade evaluation criteria by visual examination for weeding activity and crop safety (i.e. phytotoxicity) are listed in Table 2.

TABLE 2

The evaluation criteria for the phytotoxicity and weeding activity

| Grade number | Phytotoxocity (%) | Evaluation of activity on testing weeds by symptoms (suppression, abnormality, albinism, etc.) | Evaluation of crop safety based on injury to crops (suppression, abnormality, albinism, etc.) |
|---|---|---|---|
| 0 | 0 | same as control, no activity, shall be eliminated | same as control, tolerance, normal |
| 1 | 10–20 | very slight activity, shall be eliminated | very slight, can be considered |
| 2 | 30–40 | slight activity, be eliminated | slight, visual injury, shall be eliminated |
| 3 | 50–60 | moderate but insufficient activity, can be further improved | more susceptible, heavy injury, shall be eliminated |
| 4 | 70–80 | good activity, can be considered, | very susceptible, heavy injury, shall be eliminated |
| 5 | 90–100 | better activity, good compound | very susceptible, heavy injury, shall be eliminated |

Example 8

Test for Herbicidal Activities of Post-emergency Treatment

In the pots (9.5 cm diameter) containing testing soil, the seeds of *Echinochloa crusgalli, Digitaria sanguinalis, Eleusine indica, Brassica juncea, Amaranthus retroflexus* and *Portulaca oleracea* are seeded, respectively and covered with soil of 0.5 cm thick. The pots are placed into a greenhouse and the seeds are incubated for 10 days at 20–25° C. When the plants grow to two-leaf stage, the formulation obtained according to Example 2 is diluted with water, and sprayed on the stem and leaves of plants incubated above in a dosage of 750 g ai/ha. The visual injury and growth state of the individual plants is observed in regular intervals. The weeding activity of the compounds is evaluated by visual examination. The specific results are shown in Table 3.

TABLE 3

The evaluation of weeding activity for post-emergency treatment on stem and leaves

| Compound No. | No. by ZCIRI* | Dosage (g ai/ha) | Echinochlea Crusgalli | Digitaria sanguinalis | Eleusine indica | Brassica Juncea | Amaranthus retroflexus | Portulaca Oleracea |
|---|---|---|---|---|---|---|---|---|
| I-3 | ZJ0679 | 750 | 4 | 3 | 5 | 4 | 5 | 4 |
| I-4 | ZJ0685 | 750 | 5 | 3 | 5 | 5 | 5 | 4 |
| I-5 | ZJ0692 | 750 | 0 | 0 | 0 | 0 | 3 | 0 |
| I-20 | ZJ0269 | 750 | 5 | 5 | 5 | 5 | 5 | 5 |
| I-21 | ZJ0353 | 750 | 4 | 4 | 4 | 4 | 5 | 5 |
| I-22 | ZJ0354 | 750 | 2 | 0 | 3 | 0 | 4 | 0 |
| I-23 | ZJ0355 | 750 | 0 | 0 | 0 | 0 | 4 | 3 |
| I-31 | ZJ0271 | 750 | 5 | 5 | 5 | 5 | 5 | 5 |
| I-45 | ZJ0360 | 750 | 3 | 3 | 4 | 0 | 4 | 0 |
| I-46 | ZJ0361 | 750 | 5 | 5 | 5 | 4 | 5 | 5 |
| I-75 | ZJ0754 | 750 | 4 | 4 | 4 | 5 | 5 | 5 |
| I-76 | ZJ0700 | 750 | 5 | 5 | 5 | 5 | 4 | 4 |
| I-77 | ZJ0701 | 750 | 5 | 4 | 5 | 5 | 5 | 4 |
| I-78 | ZJ0273 | 750 | 5 | 5 | 5 | 5 | 5 | 5 |
| I-79 | ZJ0702 | 750 | 5 | 5 | 5 | 5 | 5 | 4 |
| I-80 | ZJ0736 | 750 | 4 | 4 | 4 | 4 | 5 | 4 |
| I-81 | ZJ0741 | 750 | 4 | 3 | 4 | 4 | 5 | 4 |
| I-82 | ZJ0738 | 750 | 4 | 4 | 4 | 4 | 5 | 4 |
| I-83 | ZJ0737 | 750 | 4 | 4 | 4 | 4 | 5 | 3 |
| I-85 | ZJ0740 | 750 | 4 | 4 | 4 | 4 | 5 | 4 |
| I-86 | ZJ0755 | 750 | 5 | 5 | 5 | 5 | 5 | 5 |
| I-87 | ZJ0756 | 750 | 5 | 4 | 5 | 5 | 5 | 5 |
| I-90 | ZJ0742 | 750 | 5 | 4 | 5 | 5 | 5 | 4 |
| I-91 | ZJ0743 | 750 | 4 | 4 | 4 | 5 | 4 | 4 |
| I-92 | ZJ0747 | 750 | 4 | 4 | 5 | 5 | 5 | 4 |
| I-93 | ZJ0746 | 750 | 4 | 4 | 4 | 4 | 5 | 4 |
| I-94 | ZJ0745 | 750 | 4 | 4 | 4 | 4 | 5 | 4 |
| I-95 | ZJ0744 | 750 | 4 | 4 | 5 | 4 | 5 | 4 |
| I-96 | ZJ0748 | 750 | 4 | 4 | 5 | 5 | 5 | 4 |
| I-97 | ZJ0749 | 750 | 4 | 4 | 5 | 5 | 5 | 4 |
| I-98 | ZJ0750 | 750 | 5 | 4 | 4 | 5 | 5 | 5 |
| I-99 | ZJ0751 | 750 | 4 | 3 | 4 | 5 | 5 | 4 |
| I-100 | ZJ0752 | 750 | 4 | 4 | 4 | 5 | 5 | 5 |
| I-101 | ZJ0859 | 750 | 5 | 5 | 4 | 5 | 5 | 4 |
| I-102 | ZJ0860 | 750 | 5 | 5 | 4 | 4 | 5 | 4 |
| I-103 | ZJ0861 | 750 | 4 | 5 | 4 | 4 | 5 | 4 |
| I-110 | ZJ0270 | 750 | 4 | 5 | 5 | 4 | 5 | 5 |
| I-120 | ZJ0358 | 750 | 4 | 4 | 4 | 0 | 5 | 5 |
| I-121 | ZJ0359 | 750 | 0 | 0 | 3 | 0 | 4 | 0 |

Example 9

Test for Weeding Activity of Pre-emergency Treatment on Soil

In the pots (9.5 cm diameter) containing testing soil, the seeds of *Echinochloa crusgalli, Digitaria sanguinalis, Eleusine indica, Brassica juncea, Amaranthus retroflexus* and *Portulaca oleracea* are seeded respectively, and covered with 0.5 cm thick soil. After 12 hours, the formulation obtained according to Example 5 is diluted with water, and applied in a dosage of 750 g ai/ha to the surface of soil which have planted the above seeds. The visual injury and growth state of the individual plants is observed in regular intervals. The weeding activity of the compounds is evaluated by 5-grade visual examination method. The specific results are shown in Table 4.

leaf or broadleaf weeds grow to two-euphylla stage in three different dosages with the formulation obtained according to the Example 5 which have been diluted into three different concentrations with water. The visual observations are made after the treatment in regular time intervals. The evaluation for the weeding activity of the compounds is made by 5-grade visual examination. The specific testing results are shown in Table 5; and the results of evaluating the weeding activities of some compounds to the susceptible *Alopecurus aequalis* are shown in Table 6.

TABLE 4

The evaluation for the weeding activity of pre-emergency treatment

| Compound No. | No. by ZCIRI* | Dosage (g ai/ha) | Echinochlea Crusgalli | Digitaria sanguinalis | Eleusine indica | Brassica Juncea | Amaranthus retroflexus | Portulaca Oleracea |
|---|---|---|---|---|---|---|---|---|
| I-3 | ZJ0679 | 750 | 3 | 3 | 4 | 5 | 4 | 4 |
| I-4 | ZJ0685 | 750 | 3 | 3 | 5 | 5 | 4 | 4 |
| I-5 | ZJ0692 | 750 | 0 | 0 | 0 | 4 | 4 | 4 |
| I-20 | ZJ0269 | 750 | 4 | 4 | 5 | 4 | 5 | 5 |
| I-21 | ZJ0353 | 750 | 4 | 4 | 5 | 0 | 5 | 5 |
| I-22 | ZJ0354 | 750 | 0 | 0 | 2 | 0 | 2 | 0 |
| I-23 | ZJ0355 | 750 | 0 | 0 | 0 | 0 | 0 | 0 |
| I-31 | ZJ0271 | 750 | 5 | 5 | 5 | 4 | 5 | 5 |
| I-45 | ZJ0360 | 750 | 0 | 0 | 3 | 0 | 0 | 0 |
| I-46 | ZJ0361 | 750 | 4 | 5 | 5 | 2 | 5 | 5 |
| I-75 | ZJ0754 | 750 | 3 | 3 | 3 | 3 | 4 | 4 |
| I-76 | ZJ0700 | 750 | 5 | 5 | 5 | 5 | 4 | 4 |
| I-77 | ZJ0701 | 750 | 5 | 5 | 5 | 5 | 5 | 5 |
| I-78 | ZJ0273 | 750 | 5 | 5 | 5 | 4 | 5 | 5 |
| I-79 | ZJ0702 | 750 | 5 | 4 | 4 | 5 | 4 | 4 |
| I-80 | ZJ0736 | 750 | 3 | 3 | 3 | 4 | 4 | 4 |
| I-81 | ZJ0741 | 750 | 4 | 3 | 3 | 4 | 4 | 3 |
| I-82 | ZJ0738 | 750 | 3 | 3 | 3 | 3 | 4 | 4 |
| I-83 | ZJ0737 | 750 | 3 | 3 | 3 | 3 | 4 | 4 |
| I-85 | ZJ0740 | 750 | 2 | 3 | 3 | 3 | 3 | 4 |
| I-86 | ZJ0755 | 750 | 4 | 4 | 3 | 4 | 4 | |
| I-87 | ZJ0756 | 750 | 4 | 4 | 3 | 4 | 4 | 4 |
| I-90 | ZJ0742 | 750 | 4 | 4 | 3 | 4 | 4 | 4 |
| I-91 | ZJ0743 | 750 | 4 | 4 | 4 | 4 | 4 | 5 |
| I-92 | ZJ0747 | 750 | 4 | 4 | 3 | 4 | 4 | 4 |
| I-93 | ZJ0746 | 750 | 4 | 4 | 3 | 4 | 4 | 4 |
| I-94 | ZJ0745 | 750 | 4 | 4 | 3 | 4 | 4 | 4 |
| I-95 | ZJ0744 | 750 | 4 | 4 | 3 | 4 | 4 | 4 |
| I-96 | ZJ0748 | 750 | 4 | 4 | 3 | 4 | 4 | 4 |
| I-97 | ZJ0749 | 750 | 4 | 4 | 4 | 4 | 4 | 5 |
| I-98 | ZJ0750 | 750 | 4 | 4 | 4 | 4 | 4 | 5 |
| I-99 | ZJ0751 | 750 | 3 | 3 | 3 | 4 | 4 | 4 |
| I-100 | ZJ0752 | 750 | 3 | 3 | 3 | 4 | 4 | 4 |
| I-101 | ZJ0859 | 750 | 4 | 4 | 4 | 5 | 5 | 5 |
| I-102 | ZJ0860 | 750 | 4 | 4 | 4 | 4 | 4 | 4 |
| I-103 | ZJ0861 | 750 | 4 | 4 | 4 | 5 | 5 | 5 |
| I-110 | ZJ0270 | 750 | 5 | 4 | 5 | 4 | 5 | 4 |
| I-120 | ZJ0358 | 750 | 0 | 2 | 4 | 0 | 0 | 0 |
| I-121 | ZJ0359 | 750 | 0 | 0 | 0 | 0 | 0 | 0 |

Example 10

The Dosage Gradient Test on Weeds by Post-emergency Treatment on Stem and Leaves The gradient tests with different dosages are conducted by taking *Echinochloa crusgalli, Digitaria sanguinalis, Eleusine indica, Brassica juncea, Amaranthus retroflexus* and *Portulaca oleracea* as testing targets. The plants are spraying treated when the Gramineae weeds grow to two-

TABLE 5

The evaluation for weeding activities of the post-emergency treatment on stem and leaves with different dosages of herbicidal compounds

| Compound No. | No. by ZCIRI* | Dosage (g ai/ha) | Echinochlea Crusgalli | Digitaria sanguinalis | Eleusine indica | Brassica Juncea | Amaranthus retroflexus | Portulaca Oleracea |
|---|---|---|---|---|---|---|---|---|
| I-3 | ZJ0679 | 75 | 0 | 0 | 0 | 0 | 3 | 0 |
|  |  | 150 | 0 | 0 | 0 | 3 | 4 | 0 |
|  |  | 300 | 2 | 0 | 2 | 3 | 4 | 3 |
| I-4 | ZJ0685 | 75 | 3 | 0 | 2 | 0 | 0 | 0 |
|  |  | 150 | 3 | 0 | 5 | 3 | 0 | 0 |
|  |  | 300 | 5 | 0 | 5 | 3 | 0 | 0 |
| I-46 | ZJ0361 | 120 | 4 | 3 | 2 | 3 | 3 | 2 |
|  |  | 245 | 5 | 5 | 4 | 3 | 3 | 1 |
|  |  | 375 | 5 | 5 | 4 | 4 | 4 | 3 |
| I-75 | ZJ0754 | 75 | 2 | 0 | 3 | 0 | 3 | 0 |
|  |  | 300 | 4 | 3 | 4 | 0 | 4 | 3 |
| I-76 | ZJ0700 | 75 | 0 | 0 | 2 | 2 | 2 | 0 |
|  |  | 150 | 3 | 0 | 3 | 3 | 4 | 0 |
|  |  | 300 | 3 | 0 | 4 | 3 | 4 | 0 |
| I-77 | ZJ0701 | 75 | 0 | 0 | 0 | 0 | 2 | 0 |
|  |  | 150 | 3 | 0 | 3 | 0 | 4 | 0 |
|  |  | 300 | 4 | 2 | 4 | 3 | 4 | 0 |
| I-78 | ZJ0273 | 75 | 0 | 0 | 2 | 1 | 5 | 5 |
|  |  | 150 | 5 | 3 | 5 | 1 | 5 | s |
|  |  | 375 | 4 | 5 | 4 | 2 | 5 | 5 |
| I-79 | ZJ0702 | 75 | 0 | 0 | 0 | 0 | 3 | 0 |
|  |  | 150 | 2 | 1 | 3 | 0 | 4 | 0 |
|  |  | 300 | 4 | 3 | 4 | 3 | 5 | 0 |
| I-80 | ZJ0736 | 75 | 0 | 0 | 0 | 0 | 4 | 0 |
|  |  | 150 | 4 | 3 | 4 | 0 | 5 | 4 |
| I-81 | ZJ0741 | 75 | 2 | 0 | 0 | 0 | 3 | 0 |
|  |  | 300 | 4 | 2 | 4 | 0 | 4 | 3 |
| I-82 | ZJ0738 | 75 | 3 | 0 | 3 | 0 | 4 | 0 |
|  |  | 300 | 4 | 4 | 5 | 2 | 5 | 3 |
| I-83 | ZJ0737 | 75 | 3 | 0 | 3 | 0 | 4 | 0 |
|  |  | 150 | 4 | 3 | 4 | 0 | 4 | 2 |
|  |  | 225 | 4 | 4 | 4 | 0 | 5 | 3 |
| I-85 | ZJ0740 | 75 | 2 | 0 | 0 | 0 | 4 | 0 |
|  |  | 150 | 3 | 0 | 3 | 0 | 4 | 0 |
|  |  | 300 | 4 | 3 | 4 | 0 | 4 | 3 |
| I-86 | ZJ0755 | 75 | 2 | 0 | 2 | 0 | 4 | 0 |
|  |  | 300 | 4 | 3 | 4 | 3 | 4 | 4 |
| I-87 | ZJ0756 | 75 | 2 | 0 | 0 | 0 | 4 | 0 |
|  |  | 150 | 4 | 2 | 3 | 0 | 4 | 2 |
|  |  | 300 | 4 | 4 | 4 | 0 | 4 | 4 |
| I-90 | ZJ0742 | 75 | 2 | 0 | 0 | 0 | 3 | 0 |
|  |  | 300 | 4 | 2 | 4 | 3 | 4 | 4 |
| I-91 | ZJ0743 | 75 | 3 | 0 | 3 | 0 | 4 | 0 |
|  |  | 150 | 4 | 0 | 4 | 0 | 4 | 3 |
|  |  | 300 | 4 | 2 | 4 | 3 | 4 | 4 |
| I-92 | ZJ0747 | 75 | 3 | 0 | 2 | 0 | 3 | 2 |
|  |  | 300 | 4 | 2 | 4 | 3 | 4 | 4 |
| I-93 | ZJ0746 | 37.5 | 2 | 0 | 2 | 0 | 4 | 0 |
|  |  | 225 | 4 | 2 | 4 | 0 | 4 | 3 |
| I-94 | ZJ0745 | 75 | 0 | 0 | 0 | 0 | 3 | 0 |
|  |  | 225 | 4 | 3 | 4 | 0 | 4 | 3 |
| I-95 | ZJ0744 | 75 | 0 | 0 | 0 | 0 | 3 | 0 |
|  |  | 300 | 4 | 2 | 4 | 0 | 4 | 4 |
| I-96 | ZJ0748 | 75 | 2 | 0 | 0 | 0 | 4 | 0 |
|  |  | 300 | 4 | 3 | 4 | 2 | 5 | 4 |
| I-97 | ZJ0749 | 75 | 0 | 0 | 0 | 0 | 4 | 0 |
|  |  | 225 | 4 | 3 | 4 | 2 | 4 | 4 |
| I-98 | ZJ0750 | 75 | 0 | 0 | 0 | 0 | 3 | 0 |
|  |  | 300 | 4 | 3 | 4 | 2 | 4 | 3 |
| I-99 | ZJ0751 | 75 | 2 | 0 | 3 | 0 | 4 | 0 |
|  |  | 225 | 4 | 3 | 4 | 3 | 4 | 4 |
| I-100 | ZJ0752 | 75 | 2 | 0 | 3 | 0 | 4 | 0 |
|  |  | 225 | 4 | 3 | 4 | 0 | 4 | 4 |
| I-101 | ZJ0859 | 75 | 5 | 4 | 4 | 5 | 5 | 5 |
|  |  | 150 | 5 | 4 | 5 | 5 | 5 | 5 |
|  |  | 300 | 5 | 4 | 5 | 5 | 5 | 5 |
| I-102 | ZJ0860 | 75 | 5 | 4 | 4 | 5 | 5 | 5 |
|  |  | 150 | 5 | 5 | 5 | 5 | 5 | 5 |
|  |  | 300 | 5 | 5 | 5 | 5 | 5 | 5 |

TABLE 5-continued

The evaluation for weeding activities of the post-emergency treatment on stem and leaves with different dosages of herbicidal compounds

| Compound No. | No. by ZCIRI* | Dosage (g ai/ha) | Echinochlea Crusgalli | Digitaria sanguinalis | Eleusine indica | Brassica Juncea | Amaranthus retroflexus | Portulaca Oleracea |
|---|---|---|---|---|---|---|---|---|
| I-103 | ZJ0861 | 75 | 4 | 4 | 4 | 4 | 5 | 4 |
|  |  | 150 | 5 | 4 | 4 | 4 | 4 | 4 |
|  |  | 300 | 5 | 5 | 5 | 5 | 5 | 5 |
| I-110 | ZJ0270 | 75 | 0 | 0 | 2 | 0 | 5 | 5 |
|  |  | 150 | 5 | 3 | 5 | 1 | 5 | 4 |
|  |  | 375 | 4 | 5 | 4 | 2 | 4 | 4 |

TABLE 6

The weeding activities of some compounds to susceptible weed *Alopecurus aequalis*

| Compound No. | No. by ZCIRI | Dosage (g ai/ha) | Alopecurus aequalis |
|---|---|---|---|
| I-76 | ZJ0700 | 15 | 3 |
|  |  | 30 | 4 |
|  |  | 45 | 5 |
|  |  | 60 | 5 |
|  |  | 75 | 5 |
| I-77 | ZJ0701 | 15 | 4 |
|  |  | 30 | 5 |
|  |  | 45 | 5 |
|  |  | 60 | 5 |
|  |  | 75 | 5 |
| I-78 | ZJ0273 | 15 | 4 |
|  |  | 30 | 5 |
|  |  | 45 | 5 |
|  |  | 60 | 5 |
|  |  | 75 | 5 |
| I-79 | ZJ0702 | 15 | 4 |
|  |  | 30 | 5 |
|  |  | 45 | 5 |
|  |  | 60 | 5 |
|  |  | 75 | 5 |

Example 11

The Dosage Gradient Test on Weed by Pre-emergency Treatment on Soil

In the post (9.5 cm diameter) containing testing soil, the seeds of *Echinochloa crusgalli*, *Digitaria sanguinalis*, *Eleusine indica*, *Brassica juncea*, *Amaranthus retroflexus* and *Portulaca oleracea* are planted respectively, and covered with 0.5 cm thick soil. After 12 hours, the formulation obtained according to Formulating Example 5 is diluted with water and soil spraying treatment is conducted in three different dosages. The visual injury and growth state of the individual treated plants are observed in regular intervals. The evaluation for the weeding activities of the compounds is made by 5-grade visual examination. The specific testing results are shown in Table 7.

TABLE 7

The evaluation for the weeding activities of pre-emergency treatment on soil with different dosages of herbicidal compounds

| Compound No. | No. by ZCIRI* | Dosage (g ai/ha) | Echinochlea Crusgalli | Digitaria sanguinalis | Eleusine indica | Brassica Juncea | Amaranthus retroflexus | Portulaca Oleracea |
|---|---|---|---|---|---|---|---|---|
| I-3 | ZJ0679 | 75 | 0 | 0 | 0 | 1 | 4 | 0 |
|  |  | 150 | 0 | 0 | 0 | 4 | 4 | 2 |
|  |  | 300 | 2 | 0 | 0 | 5 | 4 | 3 |
| I-4 | ZJ0685 | 75 | 0 | 0 | 2 | 0 | 0 | 0 |
|  |  | 150 | 2 | 0 | 4 | 4 | 2 | 2 |
|  |  | 300 | 3 | 0 | 4 | 4 | 3 | 3 |
| I-46 | ZJ0361 | 120 | 0 | 2 | 4 | 0 | 0 | 0 |
|  |  | 245 | 2 | 2 | 4 | 0 | 0 | 0 |
|  |  | 375 | 3 | 2 | 4 | 0 | 0 | 0 |
| I-75 | ZJ0754 | 75 | 0 | 0 | 3 | 0 | 4 | 0 |
|  |  | 300 | 2 | 0 | 4 | 3 | 4 | 4 |
| I-76 | ZJ0700 | 75 | 0 | 0 | 0 | 0 | 0 | 0 |
|  |  | 150 | 0 | 0 | 4 | 0 | 0 | 0 |
|  |  | 300 | 0 | 0 | 4 | 0 | 4 | 0 |
| I-77 | ZJ0701 | 75 | 0 | 0 | 0 | 0 | 0 | 0 |
|  |  | 150 | 0 | 0 | 3 | 0 | 0 | 0 |
|  |  | 300 | 0 | 0 | 4 | 0 | 2 | 0 |

TABLE 7-continued

The evaluation for the weeding activities of pre-emergency treatment on soil with different dosages of herbicidal compounds

| | | | Weeding activity Index | | | | | |
|---|---|---|---|---|---|---|---|---|
| Compound No. | No. by ZCIRI* | Dosage (g ai/ha) | *Echinochlea Crusgalli* | *Digitaria sanguinalis* | *Eleusine indica* | *Brassica Juncea* | *Amaranthus retroflexus* | *Portulaca Oleracea* |
| I-78 | ZJ0273 | 75 | 3 | 0 | 2 | 0 | 4 | 4 |
| | | 150 | 4 | 2 | 4 | 0 | 5 | 4 |
| | | 375 | 5 | 3 | 4 | 1 | 5 | 5 |
| I-79 | ZJ0702 | 75 | 0 | 0 | 0 | 0 | 0 | 0 |
| | | 150 | 0 | 0 | 3 | 0 | 0 | 0 |
| | | 300 | 0 | 0 | 4 | 2 | 2 | 0 |
| I-80 | ZJ0736 | 75 | 0 | 2 | 4 | 3 | 4 | 2 |
| | | 150 | 3 | 2 | 4 | 3 | 5 | 5 |
| I-81 | ZJ0741 | 75 | 0 | 0 | 0 | 0 | 4 | 0 |
| | | 300 | 0 | 0 | 3 | 0 | 4 | 4 |
| I-82 | ZJ0738 | 75 | 0 | 0 | 3 | 0 | 4 | 0 |
| | | 300 | 4 | 3 | 4 | 4 | 5 | 4 |
| I-83 | ZJ0737 | 75 | 0 | 0 | 4 | 0 | 4 | 0 |
| | | 150 | 0 | 0 | 4 | 0 | 4 | 3 |
| | | 225 | 4 | 2 | 4 | 0 | 4 | 3 |
| I-85 | ZJ0740 | 75 | 0 | 0 | 0 | 0 | 4 | 0 |
| | | 150 | 0 | 0 | 3 | 0 | 4 | 0 |
| | | 300 | 0 | 0 | 4 | 0 | 4 | 3 |
| I-86 | ZJ0755 | 75 | 0 | 0 | 0 | 0 | 4 | 0 |
| | | 300 | 3 | 2 | 4 | 3 | 4 | 4 |
| I-87 | ZJ0756 | 75 | 0 | 0 | 2 | 0 | 4 | 0 |
| | | 150 | 0 | 0 | 3 | 0 | 4 | 2 |
| | | 300 | 2 | 0 | 4 | 0 | 4 | 4 |
| I-90 | ZJ0742 | 75 | 0 | 0 | 0 | 0 | 4 | 3 |
| | | 300 | 3 | 2 | 4 | 0 | 4 | 4 |
| I-91 | ZJ0743 | 75 | 0 | 0 | 0 | 0 | 4 | 0 |
| | | 150 | 0 | 0 | 0 | 0 | 4 | 0 |
| | | 300 | 3 | 2 | 2 | 2 | 4 | 4 |
| I-92 | ZJ0747 | 75 | 0 | 0 | 3 | 0 | 3 | 0 |
| | | 300 | 3 | 2 | 4 | 2 | 4 | 3 |
| I-93 | ZJ0746 | 37.5 | 0 | 0 | 3 | 0 | 4 | 2 |
| | | 225 | 4 | 2 | 4 | 3 | 4 | 4 |
| I-94 | ZJ0745 | 75 | 0 | 0 | 0 | 0 | 3 | 0 |
| | | 225 | 4 | 3 | 4 | 3 | 4 | 4 |
| I-95 | ZJ0744 | 75 | 0 | 0 | 3 | 0 | 3 | 0 |
| | | 300 | 4 | 3 | 4 | 0 | 4 | 4 |
| I-96 | ZJ0748 | 75 | 0 | 0 | 0 | 0 | 3 | 1 |
| | | 300 | 4 | 3 | 4 | 3 | 4 | 4 |
| I-97 | ZJ0749 | 75 | 0 | 0 | 3 | 0 | 4 | 2 |
| | | 225 | 3 | 3 | 4 | 0 | 4 | 4 |
| I-98 | ZJ0750 | 75 | 0 | 0 | 2 | 0 | 4 | 3 |
| | | 300 | 4 | 3 | 4 | 2 | 4 | 4 |
| I-99 | ZJ0751 | 75 | 0 | 0 | 2 | 0 | 4 | 3 |
| | | 225 | 4 | 3 | 4 | 3 | 4 | 4 |
| I-100 | ZJ0752 | 75 | 2 | 0 | 3 | 0 | 4 | 3 |
| | | 225 | 4 | 3 | 4 | 0 | 4 | 4 |
| I-101 | ZJ0859 | 75 | 1 | 1 | 1 | 1 | 3 | 3 |
| | | 150 | 1 | 1 | 1 | 1 | 3 | 3 |
| | | 300 | 2 | 2 | 2 | 1 | 3 | 1 |
| I-102 | ZJ0860 | 75 | 1 | 1 | 1 | 1 | 3 | 3 |
| | | 150 | 2 | 2 | 2 | 1 | 4 | 4 |
| | | 300 | 3 | 3 | 3 | 2 | 4 | 4 |
| I-103 | ZJ0861 | 75 | 1 | 1 | 1 | 1 | 4 | 4 |
| | | 150 | 1 | 1 | 1 | 1 | 4 | 4 |
| | | 300 | 2 | 2 | 2 | 2 | 4 | 4 |
| I-110 | ZJ0270 | 75 | 3 | 0 | 2 | 0 | 4 | 4 |
| | | 150 | 4 | 2 | 4 | 0 | 4 | 4 |
| | | 375 | 5 | 3 | 4 | 1 | 5 | 4 |

Example 12

The Evaluation for Crop Safety of Pre-emergency Treatment on Stem and Leaves

In post (diameters of 12 cm) containing test soil, the conventional or hybridized seeds of cotton, rape, soybean, corn, wheat and paddy are planted, respectively, and grown in a greenhouse at 20–25° C. After growing to a given period, the spraying treatment is conducted in different dosages by diluting the formulation obtained according to Formulating Example 5 to a given concentration. The visual injury and growth state of the individual plants are observed in regular intervals. The evaluation for the crop safety of the compounds is conducted by 5-grade visual observation. The specific testing results are shown in Table 8. The results indicate that some of the compounds are safe to crops such as rape, cotton, soybean, paddy, etc.

TABLE 8

Evaluation for crop safety of post-emergency treatment on leaves

| Compound No. | No. by ZCIRI | Dosage (g ai/ha) | Paddy | Wheat | Corn | Rape | Cotton | Soybean |
|---|---|---|---|---|---|---|---|---|
| I-76 | ZJ0700 | 150 | 3 | 0 | 1 | 1 | 2 | 1 |
|  |  | 300 | 3 | 1 | 2 | 2 | 3 | 2 |
|  |  | 450 | 4 | 1 | 3 | 3 | 4 | 2 |
| I-77 | ZJ0701 | 150 | 3 | 0 | 1 | 1 | 2 | 1 |
|  |  | 300 | 4 | 1 | 3 | 2 | 3 | 1 |
|  |  | 450 | 4 | 1 | 4 | 4 | 4 | 2 |
| I-78 | ZJ0273 | 75 | 3 | 1 | 2 | 0 | 0 | 1 |
|  |  | 150 | 4 | 3 | 3 | 1 | 0 | 2 |
|  |  | 300 | 4 | 5 | 5 | 1 | 0 | 3 |
|  |  | 450 | 5 | 5 | 5 | 2 | 1 | 3 |
| I-79 | ZJ0702 | 150 | 3 | 0 | 1 | 1 | 1 | 1 |
|  |  | 300 | 3 | 1 | 3 | 2 | 2 | 2 |
|  |  | 450 | 4 | 1 | 4 | 4 | 3 | 2 |
| I-101 | ZJ0859 | 75 | 0 | 1 | 2 | 1 | 2 | 0 |
|  |  | 150 | 0 | 3 | 3 | 1 | 2 | 0 |
|  |  | 375 | 1 | 2 | 4 | 2 | 3 | 1 |
| I-102 | ZJ0860 | 75 | 0 | 1 | 2 | 1 | 2 | 0 |
|  |  | 150 | 1 | 2 | 2 | 1 | 2 | 0 |
|  |  | 375 | 1 | 2 | 3 | 1 | 3 | 1 |
| I-103 | ZJ0861 | 75 | 0 | 1 | 2 | 1 | 1 | 1 |
|  |  | 150 | 1 | 2 | 3 | 2 | 2 | 2 |
|  |  | 375 | 1 | 3 | 4 | 3 | 2 | 3 |
| I-110 | ZJ0270 | 75 | 3 | — | — | — | — | — |
|  |  | 150 | 4 | — | — | — | — | — |
|  |  | 300 | 5 | — | — | — | — | — |

Example 13

Evaluation for Paddy Safety of Treatment on the Stem and Leaves of Transplanted Paddy Seedlings In pots (diameter of 12 cm) containing test soil, paddy seedlings of the given stage are transplanted and grown in the greenhouse at 20–30° C. After growing to 4–5-leaves stage, the spraying treatment on the stem and leaves of paddy seedlings is conducted in a dosage of 150 g ai/ha after diluting the formulation obtained according to Formulating Example 5 into a given concentration. The visual injury and growth state of the individual plants are observed in regular intervals. The evaluation for the crop safety of the compounds is conducted by 5-grade visual observation. The specific testing results are shown in Table 9.

TABLE 9

Evaluation for crop safeties of part compounds to the transplanted paddy seedlings

| Compound No. | No. by ZCIRI | Dosage (g ai/ha) | Effect on tillering | Stunting | Leaf color |
|---|---|---|---|---|---|
| I-101 | ZJ0859 | 150 | None | <10% | Recover to normal |
| I-102 | ZJ0860 | 150 | None | 10–15% | Slight yellow |
| I-103 | Zj0861 | 150 | None | 20–25% | Slight yellow |

What is claimed is:

1. A 2-pyrimidinyloxy-N-aryl-benzylamine derivative, shown by the following formula:

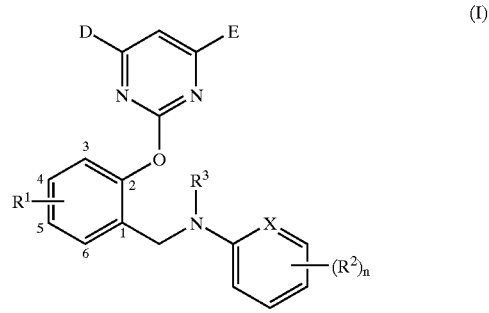

where:

D or E independently represents hydrogen, halogen, $C_1$–$C_4$ alkyl, $C_1$–$C_4$ alkoxy, $C_1$–$C_4$ haloalkyl or $C_1$–$C_4$ haloalkoxy, D and E can be same or different;

$R^1$ is hydrogen, halogen, $C_1$–$C_4$ alkyl, $C_1$–$C_4$ alkoxy, which can be at any one position of 3-, 4-, 5- and 6-positions in benzene ring;

$R^2$ is hydrogen; halogen, $C_1$–$C_4$ alkyl, $C_1$–$C_4$ alkoxy, $C_1$–$C_4$ carbamyl, $C_1$–$C_4$ alkoxycarbonyl, $C_1$–$C_4$ haloalkyl, cyano, nitro, carboxy or its alkali metal, and alkali earth metal salts, $C_1$–$C_4$ alkylamido, $C_1$–$C_4$ haloalkylamido, heterocyclic amido selected from pyridinyl amido, thiophenyl amido, thiazolyl amido, and pyrimidinyl amido; 6-(4,6-dimethoxy-2-pyrimidinyl)oxy, benzamido optionally substituted by a constituent selected from the group consisting of halogen, $C_1$–$C_4$ alkyl, $C_1$–$C_4$ alkoxy, trifluoromethyl, cyano, nitro group located at m-, o- or p-position, or a benzo or bromo benzo compound, wherein $R^2$ can be located at m-, o- or p-position of a benzene ring, n=1–3;

$R^3$ is hydrogen, $C_1$–$C_4$ alkanoyl, $C_1$–$C_4$ haloalkanoyl, benzoyl or $C_1$–$C_4$ alkoxyacetyl; and X is CH or N.

2. The 2-pyrimidinyloxy-N-aryl-benzylamine derivative of claim 1, characterized in that both of D and E are methoxy.

3. The 2-pyrimidinyloxy-N-aryl-benzylamine derivative of claim 1, characterized in that $R^2$ is trifluoroformamido, halogen located in o-, m- or p-position, $C_1$–$C_4$ alkyl, $C_1$–$C_4$ alkyloxy, trifluoromethyl, cyano, or nitro substituted benzamido, methyl, methoxy, trifluoromethyl, $C_1$–$C_4$ alkoxycarbonyl, carboxy or its sodium, potassium and ammonium salt.

4. The 2-pyrimidinyloxy-N-aryl-benzylamine derivative of claim 1, characterized in that $R^3$ is hydrogen, acetyl, chloroacetyl, dichloroacetyl, benzoyl or methoxyacetyl.

5. A process for preparing the 2-pyrimidinyloxy-N-aryl-benzylamine derivative formula (1) of claim 1, characterized in that the intermediate (II) is obtained by reacting salicylal, aromatic amine and a catalyst with molar ratio of 1:(1–2):(0–0.2) for 0.5–12 hours in an organic solvent at a temperature from room temperature to the boiling point of solvent, the said catalyst is p-methyl benzenesulfonic acid, methanesulfonic acid, sulfuric acid, hydrochloric acid or acetic acid;

reacting the intermediate (II) and a reductant with molar ratio of 1:(0.5–2) for 0.5–10 hours in an organic solvent at a reaction temperature in the range of room temperature to 40° C. to give the intermediate (III), the said reductant is sodium borohydride or potassium borohydride; reducing compound (II) with hydrogen in an organic solvent at a reaction temperature between room temperature and 40° C. to give the intermediate (III), wherein the catalyst is Raney Nickel, palladium-carbon and platinum black, the molar ratio between reactant (II) and the catalyst is 1:(0.01–0.05), the reaction temperature is 0.5–10 hours;

reacting the intermediate (III) with 2-methylsulfonyl-4-D, 6-E-substituted pyrimidine for 0.5–20 hours in an organic solvent at a reaction temperature between room temperature and the boiling point of the solvent, to give 2-pyrimidinyloxy-N-aryl-benzylamine ($R^3$=H), wherein the molar ratio of the intermediate (III) to 2-methylsulfonyl-4-d, 6-E-substituted pyrimidine to base is 1:(1.0–1.2):(1–5), the said base is monovalent or divalent metal hydrides, alkoxides or carbonates, or organobase;

reacting the mixture of the compound 2-pyrimidinyloxy-N-aryl-benzylamine (I, $R^3$=H) shown by the above formula (I, $R^3$=H), an acid anhydride or an acid chloride $R^3Cl$ ($R^3$ H) and a base with a molar ratio of 1:(1.0–4.0):(0–2) for 2–8 hours under reflux condition, to form the compound of formula (I) ($R^3$ H), wherein, the intermediates (II), (III) or the compound of formula (I) are shown by the following formulas:

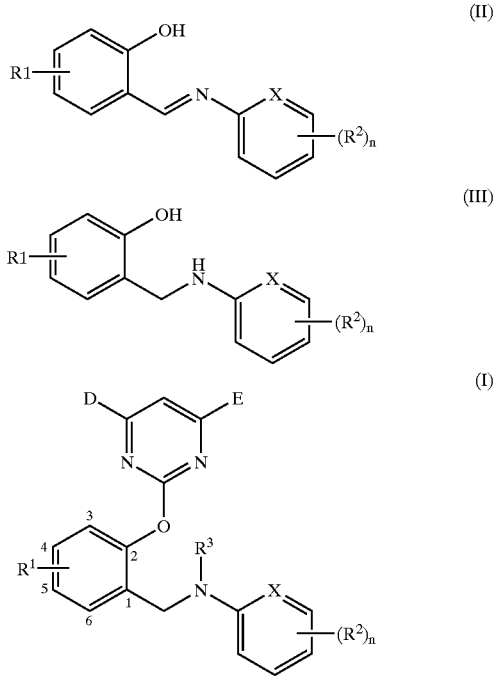

6. A process for preparing 2-pyrimidinyloxy-N-aryl-benzylamine derivative according to claim 4 characterized in that the final product is purified by chromatography on silica gel column or recrystallization.

7. A process for preparing 2-pyrimidinyloxy-N-aryl-benzylamine derivative according to claim 4 characterized in that the molar ratio of the said catalyst to aromatic amine is (0.01–0.1):1 when preparing the intermediate (II).

8. A process for preparing the 2-pyrimidinyloxy-N-aryl-benzylamine derivative according to claim 4 characterized in that the said hydrides and alkoxides of the said monovalent or divalent metals are sodium hydride, potassium hydride, calcium hydride, sodium methoxide, sodium ethoxide, potassium methoxide, potassium ethoxide, sodium carbonate, potassium carbonate or calcium carbonate.

9. The process of claim 5, wherein the organobase is triethylamine and pyridine.

10. Use of an effective amount of the 2-pyrimidinyloxy-N-aryl-benzylamine derivative of claim 1, characterized in that it comprises a step of directly or indirectly applying the derivative to a crop, wherein, the 2-pyrimidinyloxy-N-aryl-benzylamine derivative is of the following formula:

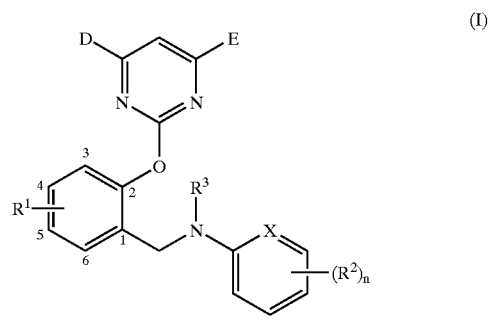

where:

D or E independently represents hydrogen, halogen, $C_1$–$C_4$ alkyl, $C_1$–$C_4$ alkoxy, $C_1$–$C_4$ haloalkyl or $C_1$–$C_4$ haloalkoxy, D and E can be same or different;

$R^1$ is hydrogen, halogen, $C_1$–$C_4$ alkyl, $C_1$–$C_4$ alkoxy, which can be at any one position of 3-, 4-, 5- and 6-positions in the benzene ring;

$R^2$ is hydrogen; halogen; $C_1$–$C_4$ alkyl, $C_1$–$C_4$ alkoxy; $C_1$–$C_4$ carbamyl; $C_1$–$C_4$ alkoxycarbonyl; $C_1$–$C_4$ haloalkyl; cyano; nitro; carboxy or its alkali metal, and alkali earth metal salts; $C_1$–$C_4$ alkylamido; $C_1$–$C_4$ haloalkylamido; heterocyclic amido selected from the group consisting of pyridinyl amido, thiophenyl amido, thiazolyl amido and pyrimidinyl amido; 6-(4,6-dimethoxy-2-pyrimidinyl)oxy; benzamido optionally substituted by halogen, $C_1$–$C_4$ alkyl, $C_1$–$C_4$ alkoxy, trifluoromethyl, cyano, nitro group located at m-, o- or p-position; and a benzo or bromo benzo compound; wherein $R^2$ can be located at m-, o- or p-position of a benzene ring, n=1–3;

$R^3$ is hydrogen, $C_1$–$C_4$ alkanoyl, $C_1$–$C_4$ haloalkanoyl, benzoyl or $C_1$–$C_4$ alkoxyacetyl; and X is CH or N.

* * * * *

UNITED STATES PATENT AND TRADEMARK OFFICE
CERTIFICATE OF CORRECTION

PATENT NO.          : 6,800,590 B2
APPLICATION NO. : 10/380865
DATED                 : October 5, 2004
INVENTOR(S)       : Lu et al.

It is certified that error appears in the above-identified patent and that said Letters Patent is hereby corrected as shown below:

Column 4, line 5:
"X is H or N, preferably H."

should be:
--X is CH or N, preferably CH.

Columns 4 and 5, Table 1, please replace Table 1 as follows:

TABLE 1. 2-pyrimidinyloxy-$N$-aryl-benzylamine derivatives

| Compound No. | D=E | $R^1$ | $R^2$ |  | $R^3$ | X |
|---|---|---|---|---|---|---|
| 1-1 | $OCH_3$ | H | H | | H | CH |
| 1-2 | $OCH_3$ | 6-Cl | H | | H | CH |
| 1-3 | $OCH_3$ | 5-F | H | | H | CH |
| 1-4 | $OCH_3$ | 5-$OCH_3$ | H | | H | CH |
| 1-5 | $OCH_3$ | 5-Cl | H | | H | CH |

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

TABLE 1 -continued

| 1-6  | OCH₃ | H    | 2-F  | H           | CH |
|------|------|------|------|-------------|----|
| 1-7  | OCH₃ | H    | 2-F  | -COCH₂OCH₃  | CH |
| 1-8  | OCH₃ | H    | 2-F  | -COCH₂Cl    | CH |
| 1-9  | OCH₃ | H    | 3-F  | -COCH₂Cl    | CH |
| 1-10 | OCH₃ | 6-Cl | 4-F  | H           | CH |
| 1-11 | OCH₃ | H    | 2-Cl | H           | CH |
| 1-12 | OCH₃ | H    | 2-Cl | -COCH₂Cl    | CH |
| 1-13 | OCH₃ | H    | 3-Cl | H           | CH |
| 1-14 | OCH₃ | H    | 3-Cl | -COCH₂Cl    | CH |
| 1-15 | OCH₃ | H    | 3-Cl | -COCH₂OCH₃  | CH |
| 1-16 | OCH₃ | H    | 4-Cl | H           | CH |
| 1-17 | OCH₃ | H    | 4-Cl | -COCH₂Cl    | CH |
| 1-18 | OCH₃ | H    | 4-Cl | -COCH₂OCH₃  | CH |

UNITED STATES PATENT AND TRADEMARK OFFICE
CERTIFICATE OF CORRECTION

PATENT NO.         : 6,800,590 B2
APPLICATION NO. : 10/380865
DATED                  : October 5, 2004
INVENTOR(S)       : Lu et al.

It is certified that error appears in the above-identified patent and that said Letters Patent is hereby corrected as shown below:

TABLE 1 -continued

| 1-19 | OCH₃ | 3-OCH₃ | 2-Br | H | CH |
|---|---|---|---|---|---|
| 1-20 | OCH₃ | H | 4-Br | H | CH |
| 1-21 | OCH₃ | H | 4-Br | -CO(CH₂)₃Cl | CH |
| 1-22 | OCH₃ | H | 4-Br | -CO(C₆H₅) | CH |
| 1-23 | OCH₃ | H | 4-Br | -COCHCl₂ | CH |
| 1-24 | OCH₃ | H | 4-Br | -COCH₂CH₃ | CH |
| 1-25 | OCH₃ | H | 4-Br | -COCHCl₂ | CH |
| 1-26 | OCH₃ | H | 2-I | H | CH |
| 1-27 | OCH₃ | H | 2-I | -COCH₂Cl | CH |
| 1-28 | OCH₃ | H | 3-I | H | CH |
| 1-29 | OCH₃ | H | 3-I | -COCH₂Cl | CH |
| 1-30 | OCH₃ | H | 3-I | -COCH₂OCH₃ | CH |
| 1-31 | OCH₃ | H | 4-I | H | CH |

UNITED STATES PATENT AND TRADEMARK OFFICE
CERTIFICATE OF CORRECTION

PATENT NO.      : 6,800,590 B2
APPLICATION NO. : 10/380865
DATED           : October 5, 2004
INVENTOR(S)     : Lu et al.

It is certified that error appears in the above-identified patent and that said Letters Patent is hereby corrected as shown below:

TABLE 1 -continued

| | | | | | |
|---|---|---|---|---|---|
| 1-32 | $OCH_3$ | H | 4-I | $-COCH_2Cl$ | CH |
| 1-33 | $OCH_3$ | H | 4-I | $-COCHCl_2$ | CH |
| 1-34 | $OCH_3$ | H | 4-I | $-COCH_3$ | CH |
| 1-35 | $OCH_3$ | H | 4-I | $-COCH_2OCH_3$ | CH |
| 1-36 | $OCH_3$ | H | $2-CH_3$ | H | CH |
| 1-37 | $OCH_3$ | H | $2-CH_3$ | $-COCH_2Cl$ | CH |
| 1-38 | $OCH_3$ | H | $4-CH_3$ | H | CH |
| 1-39 | $OCH_3$ | H | $4-CH_3$ | $-COCH_2Cl$ | CH |
| 1-40 | $OCH_3$ | H | $2-CF_3$ | H | CH |
| 1-41 | $OCH_3$ | H | $2-CF_3$ | $-COCH_2Cl$ | CH |
| 1-42 | $OCH_3$ | H | $4-CF_3$ | H | CH |
| 1-43 | $OCH_3$ | H | $4-CF_3$ | $-COCH_2Cl$ | CH |

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

TABLE 1 -continued

| 1-44 | OCH$_3$ | H | 4-OCH$_3$ | H | CH |
| 1-45 | OCH$_3$ | H | 4-OCH$_3$ | -COCHCl$_2$ | CH |
| 1-46 | OCH$_3$ | H | 4-OCH$_3$ | -CO(CH$_2$)$_3$Cl | CH |
| 1-47 | OCH$_3$ | H | 3,4-di-F | H | CH |
| 1-48 | OCH$_3$ | H | 2,5- di-Cl | H | CH |
| 1-49 | OCH$_3$ | H | 2,5-di-Cl | -COCH$_2$Cl | CH |
| 1-50 | OCH$_3$ | H | 2,3-di-Cl | H | CH |
| 1-51 | OCH$_3$ | H | 2,3-di-Cl | -COCH$_2$Cl | CH |
| 1-52 | OCH$_3$ | H | 3,4-di-Cl | H | CH |
| 1-53 | OCH$_3$ | H | 3,4-di-Cl | -COCH$_2$Cl | CH |
| 1-54 | OCH$_3$ | H | 3,4-di-Cl | -COCH$_2$OCH$_3$ | CH |
| 1-55 | OCH$_3$ | 3-OCH$_3$ | 3,4-di-Cl | H | CH |
| 1-56 | OCH$_3$ | H | 3,5-di-Cl | H | CH |
| 1-57 | OCH$_3$ | H | 3,5-di-Cl | -COCH$_2$Cl | CH |

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

TABLE 1 -continued

| 1-58 | OCH$_3$ | H | 2,4-di-Cl | H | CH |
| 1-59 | OCH$_3$ | H | 2,4-di-Cl | -COCH$_2$Cl | CH |
| 1-60 | OCH$_3$ | H | 2,4-di-Cl-3-F | H | CH |
| 1-61 | OCH$_3$ | 3-OCH$_3$ | 2,4-di-Cl-3-F | H | CH |
| 1-62 | OCH$_3$ | H | 2-F-4-Br | H | CH |
| 1-63 | OCH$_3$ | 3-OCH$_3$ | 2-F-4-Br | H | CH |
| 1-64 | OCH$_3$ | H | 2-CH$_3$-5-Cl | H | CH |
| 1-65 | OCH$_3$ | H | 2-CH$_3$-5-Cl | -COCH$_2$Cl | CH |
| 1-66 | OCH$_3$ | H | 2-CH$_3$-3-Cl | H | CH |
| 1-67 | OCH$_3$ | H | 2,4-di-CH$_3$ | H | CH |
| 1-68 | OCH$_3$ | H | 2,4-di-CH$_3$ | -COCH$_2$Cl | CH |
| 1-69 | OCH$_3$ | H | 3,4-di-CH$_3$ | H | CH |
| 1-70 | OCH$_3$ | H | 2,6-di-CH$_2$CH$_3$ | H | CH |

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

TABLE 1 -continued

| 1-71 | $OCH_3$ | H | 3,4-di-$CH_3$ | -$COCH_2Cl$ | CH |
| --- | --- | --- | --- | --- | --- |
| 1-72 | $OCH_3$ | H | 2,6-di-$CH_2CH_3$ | -$COCH_2Cl$ | CH |
| 1-73 | $OCH_3$ | H | 2-Cl-5-$CF_3$ | H | CH |
| 1-74 | $OCH_3$ | H | 2-Cl-5-$CF_3$ | -$COCH_2Cl$ | CH |
| 1-75 | $OCH_3$ | H | 4-$NO_2$ | H | CH |
| 1-76 | $OCH_3$ | H | 4-$CO_2CH_3$ | H | CH |
| 1-77 | $OCH_3$ | H | 4-$CO_2CH_2CH_3$ | H | CH |
| 1-78 | $OCH_3$ | H | 4-$CO_2CH_2CH_2CH_3$ | H | CH |
| 1-79 | $OCH_3$ | H | 4-$CO_2CH(CH_3)2$ | H | CH |
| 1-80 | $OCH_3$ | H | 4-$CO_2CH_2CH_2CH_2CH_3$ | H | CH |
| 1-81 | $OCH_3$ | H | 4-$CO_2C(CH_3)_3$ | H | CH |
| 1-82 | $OCH_3$ | H | 4-$CO_2CH_2CH(CH_3)_2$ | H | CH |
| 1-83 | $OCH_3$ | H | 4-$CO_2CH_2CF_3$ | H | CH |

UNITED STATES PATENT AND TRADEMARK OFFICE
CERTIFICATE OF CORRECTION

PATENT NO. : 6,800,590 B2  Page 8 of 17
APPLICATION NO. : 10/380865
DATED : October 5, 2004
INVENTOR(S) : Lu et al.

It is certified that error appears in the above-identified patent and that said Letters Patent is hereby corrected as shown below:

TABLE 1 -continued

| | | | | | |
|---|---|---|---|---|---|
| 1-84 | OCH$_3$ | H | 4-CO$_2$CH$_2$CF$_2$CF$_2$H | H | CH |
| 1-85 | OCH$_3$ | H | 4-CO$_2$CH(CF$_3$)$_2$ | H | CH |
| 1-86 | OCH$_3$ | H | 4-CO$_2$CH$_2$C≡CH | H | CH |
| 1-87 | OCH$_3$ | H | 4-CO$_2$CH$_2$CH=CH$_2$ | H | CH |
| 1-88 | OCH$_3$ | 5-n-C$_9$H$_{19}$ | 4-CO$_2$CH$_2$CH$_2$CH$_3$ | H | CH |
| 1-89 | OCH$_3$ | 3-OCH$_3$ | 4-CO$_2$CH$_2$CH$_2$CH$_3$ | H | CH |
| 1-90 | OCH$_3$ | H | 2-CO$_2$CH$_3$ | H | CH |
| 1-91 | OCH$_3$ | H | 2-CO$_2$CH$_2$CH$_3$ | H | CH |
| 1-92 | OCH$_3$ | H | 2-CO$_2$CH$_2$CH$_2$CH$_3$ | H | CH |
| 1-93 | OCH$_3$ | H | 3-CO$_2$CH$_3$ | H | CH |
| 1-94 | OCH$_3$ | H | 3-CO$_2$CH$_2$CH$_3$ | H | CH |
| 1-95 | OCH$_3$ | H | 3-CO$_2$CH$_2$CH$_2$CH$_3$ | H | CH |
| 1-96 | OCH$_3$ | H | 3-CO$_2$CH(CH$_3$)$_2$ | H | CH |

UNITED STATES PATENT AND TRADEMARK OFFICE
CERTIFICATE OF CORRECTION

PATENT NO.      : 6,800,590 B2
APPLICATION NO. : 10/380865
DATED           : October 5, 2004
INVENTOR(S)     : Lu et al.

It is certified that error appears in the above-identified patent and that said Letters Patent is hereby corrected as shown below:

TABLE 1 -continued

| 1-97  | OCH$_3$ | H       | 4-CON(CH$_2$CH$_3$)$_2$      | H  | CH |
|-------|---------|---------|------------------------------|----|----|
| 1-98  | OCH$_3$ | H       | 4-CONHCH$_2$CH$_2$CH$_3$     | H  | CH |
| 1-99  | OCH$_3$ | H       | 4-CONHCH$_2$CH$_2$CH$_2$CH$_3$ | H | CH |
| 1-100 | OCH$_3$ | H       | 4-CO$_2$H                    | H  | CH |
| 1-101 | OCH$_3$ | H       | 4-NHCOCH(CH$_3$)$_2$         | H  | CH |
| 1-102 | OCH$_3$ | H       | 4-NHCO(C$_6$H$_5$)           | H  | CH |
| 1-103 | OCH$_3$ | H       | 4-NHCOCF$_3$                 | H  | CH |
| 1-104 | OCH$_3$ | H       | 4-NHCOCH$_3$                 | H  | CH |
| 1-105 | OCH$_3$ | 3-OCH$_3$ | 4-NHCOCH(CH$_3$)$_2$       | H  | CH |
| 1-106 | OCH$_3$ | 3-OCH$_3$ | 4-NHCOCH$_3$               | H  | CH |
| 1-107 | OCH$_3$ | H       | 4-NHCOCH(CH$_3$)$_2$         | Ac | CH |

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

TABLE 1 -continued

| 1-108 | OCH₃ | H | 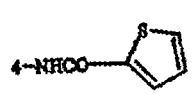 | H | CH |
| 1-109 | OCH₃ | H |  | H | CH |
| 1-110 | OCH₃ | H |  | H | CH |
| 1-111 | OCH₃ | H | 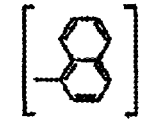 | H | CH |

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

TABLE 1 -continued

| | | | | | |
|---|---|---|---|---|---|
| 1-112 | OCH₃ | H |  | -COCH₂Cl | C̲H̲ |
| 1-113 | OCH₃ | H |  | H | C̲H̲ |
| 1-114 | OCH₃ | H | 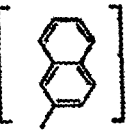 | -COCH₂Cl | C̲H̲ |
| 1-115 | OCH₃ | H | 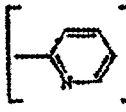 | H | N |

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

Column 11, lines 37 and 38:
"…. , X is hydro-gen or nitrogen atom."

should be:
--…., X is CH Group or nitrogen atom.--

Column 12, lines 52 through 67 and column 13, lines 1-5:
"haloacetyl, D and E, $R^1$-$R^3$ are as described above, $R^3$ in the reaction scheme is $C_1$-$C_4$ alkoxyacetyl or haloacetyl.
    To a solvent in the present of a base and at a temperature from room temperature to the reflux temperature, was added the compound (3) represented by formula (I, R=H) and an acid anhydride or acid chloride $R^3$Cl and a base with a molar ratio of 1:(1.0-4):(0-2) and stirred for 2-8 hours to give the compound represented by formula (I) (R≠H) which also has weed control activity. The solvent and base used are the same as those in the third step during the synthesis of compound (3) as shown by formula (I) (R=H) described above. When the molar ratio of the compound (3) shown by the above 2-pyrimidinyloxy-N-aryl-benzylamine (I, $R^3$=H) represented by formula (I) (R=H) to the acid anhydride or acid chloride $R^3$Cl to the base was 1:(1.0-4):(0-2), the reaction was carried out for 2-8 hours in a solvent at a temperature from room temperature to the reflux temperature, to give a compound as shown in formula (I) (R≠H), the N-acylated product of 2-pyrimidinyloxy-N-arylbenzylamine (I, $R^3$≠H)."

should be:
--haloacetyl, D and E, $R^1$-$R^2$ are as described above.
    When the molar ratio of the compound (3) represented by the above 2-pyrimidinyloxy-*N*-aryl-benzylamine (1, $R^3$=H) represented by formula (1) ($R^3$=H) to the acid anhydride or acid chloride $R^3$Cl to the base was 1 : (1.0-4) : (0-2), the reaction was carried out for 2-8 hours in a solvent in the present of a base and at a temperature from room temperature to the reflux temperature, to give a compound as shown in formula (1) $R^3$≠H), the *N*-acylated product of 2-phrimidinyloxy-*N*-aryl-benzylamine (1, $R^3$≠H). The solvent and base used are the same as those in the third step during the synthesis of compound (3) a shown by formula (1) ($R^3$=H) described above.--

Column 14, line 1:
"hydroxybenzylideneamino )benzamide. The intermediate is"

should be:
--hydroxybenzylideneamino )benzoate. The intermediate is--

UNITED STATES PATENT AND TRADEMARK OFFICE
CERTIFICATE OF CORRECTION

PATENT NO.        : 6,800,590 B2
APPLICATION NO.   : 10/380865
DATED             : October 5, 2004
INVENTOR(S)       : Lu et al.

It is certified that error appears in the above-identified patent and that said Letters Patent is hereby corrected as shown below:

Column 14, lines 10-11:
"give 22.7 g white solid 1-propyl 4- (2-hydroxy-benzylamino)benzamide. The yield in the two steps is 80%."

should be:
--give 22.7 g white solid *n*-propyl 4-(2-hydroxy-benzylamino)benzoate. The yield in the two steps is 80%.--

Column 14, line 14:
"benzylamino) benzamide…."

should be:
--benzylamino) benzoate….--

Column 14, line 22:
"benzylamino)-benzamide…."

should be:
--benzylamino)-benzoate….--

Column 14, line 38:
"hydroxybenzylideneamino)benzamide. …."

should be:
--hydroxybenzylideneamino)benzoate. …--

Column 14, line 48:
"benzamide. The…."

should be:
--benzoate. The….--

Column 14, line 50:
"benzylamino)benzamide…."

should be:
--benzylamino)benzoate….--

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

Column 14, line 58:
"pyrimidinyloxy)-benzylamino]benzamide...."

should be:
--pyrimidinyloxy)-benzylamino]benzoate.....--

Column 38, line 25-38:
"R2 is hydrogen; halogen, $C_1$-$C_4$ alkyl, $C_1$-$C_4$ alkoxy, $C_1$-$C_4$ carbamyl, $C_1$-$C_4$ alkoxycarbonyl, $C_1$-$C_4$ haloalkyl, cyano, nitro, carboxy or its alkali metal, and alkali earth metal salts, $C_1$-$C_4$ alkylamido, $C_1$-$C_4$ cyano, nitro, carboxy, or its alkali metal, and alkali earth metal salts, $C_1C_4$ alkylamido, $C_1$-$C_4$ haloalkylamido, heterocyclic amido selected from pyridinyl amido, thiophenyl amido, thiazolyl amido, and pyrimidinyl mido; 6-(4,6-dimethoxy-2-pyrimidinyl)oxy, benzamido optionally substituted by a constituent selected from the group consisting of halogen, $C_1$-$C_4$ alkyl, $C_1$-$C_4$ alkoxy, trifluoromethyl, cyano, nitro group located at m-, o-or p-position, or a benzo or bromo benzo compound, wherein $R^2$ can be located at m-, o- or p-position of a benzene ring, n=1-3;"

should be:
--R2 is hydrogen; halogen, $C_1$-$C_4$ alkyl, $C_1$-$C_4$ alkoxy, $C_1$-$C_4$ carbamyl, $C_1$-$C_4$ alkoxycarbonyl, $C_1$-$C_4$ haloalkyl, cyano, nitro, carboxy or its alkali metal, alkali earth metal and organoammonium salts, $C_1$-$C_4$ alkylamido, $C_1$-$C_4$ haloalkylamido, heterocyclic amido, benzamido or substituted benzamido, or a benzo or substituted benzo compound, wherein $R^2$ can be located at *m*-, o-or *p*-position of a benzene ring, n=1-3;--

Column 38, lines 55-Column 39, lines 1-58:
"5.    A process for preparing the 2-pyrimidinyloxy-N-aryl-benzylamine derivative formula (1) of claim 1, characterized in that the intermediate (II) is obtained by reacting salicylal, aromatic amine and a catalyst with molar ratio of 1:(1-2): (0-0.2) for 0.5-12 hours in an organic solvent at a temperature from room temperature to the boiling point of solvent, the said catalyst is p-methyl benzenesulfonic acid, methanesulfonic acid, sulfuric acid, hydrochloric acid or acetic acid;
reacting the intermediate (II) and a reductant with molar ratio of 1:(0.5-2) for 0.5-10 hours in an organic solvent at a reaction temperature in the range of room temperature to 40° C. to give the intermediate (III), the said reductant is sodium borohydride or potassium borohy-dride; reducing compound (II) with hydrogen in an organic solvent at a reaction

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

temperature between room temperature and 40° C. to give the intermediate (III), wherein the catalyst is Raney Nickel, Palladium-carbon and platinum black, the molar ratio between reactant (II) and the catalyst is 1:(0.01-0.05), the reaction temperature is 0.5-10 hours;
reacting the intermediate (III) with 2-methylsulfonyl-4-D, 6-E-substituted pyrimidine for O.5-20 hours in an organic solvent at a reaction temperature between room temperature and the boiling point of the solvent, to give 2-pyrimidinyloxy-N-aryl-benzylamine ($R^3$=H), wherein the molar ratio of the intermediate (III) to 2-methylsulfonyl-4-d, 6-E-substituted pyrimidine to base is 1:(1.0-1.2):(1-5), the said base is monovalent or divalent metal hydrides, alkoxides or carbonates, or organobase;
reacting the mixture of the compound 2-pyrimidinyloxy-N-aryl-benzylamine (I,$R^3$=H) shown by the above formula (I,$R^3$=H), an acid anhydride or an acid chloride $R^3$Cl ($R^3$ H) and a base with a molar ratio of 1:(1.0-4.0):(0-2) for 2-8 hours under reflux condition, to form the compound of formula (I) ($R^3$ H), wherein, the intermediates (II), (III) or the compound of formula (I) are shown by the following formulas:

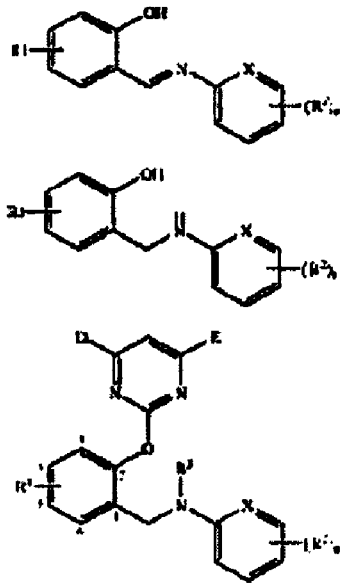

UNITED STATES PATENT AND TRADEMARK OFFICE
CERTIFICATE OF CORRECTION

| | |
|---|---|
| PATENT NO. | : 6,800,590 B2 |
| APPLICATION NO. | : 10/380865 |
| DATED | : October 5, 2004 |
| INVENTOR(S) | : Lu et al. |

It is certified that error appears in the above-identified patent and that said Letters Patent is hereby corrected as shown below:

should be:

--5. A process for preparing the 2-pyrimidinyloxy-$N$-aryl-benzylamine derivative of Claim 1, characterized in that the intermediate (II) is obtained by reacting salicylal, aromatic amine and a catalyst with molar ratio of 1 : (1-2) : (0-0.2) for 0.5-12 hours in an organic solvent at a temperature from room temperature to the boiling point of solvent, the said catalyst is $p$-methyl benzenesulfonic acid, methanesulfonic acid, sulfuric acid, hydrochloric acid or acetic acid;
    reacting the intermediate (II) and a reductant with molar ratio of 1:(0.5-2) for 0.5-10 hours in an organic solvent at a reaction temperature in the range of room temperature to 40°C to give the intermediate (III), the said reductant is sodium borohydride or potassium borohydride; reducing compound (II) with hydrogen in an organic solvent at a reaction temperature between room temperature and 40°C to give the intermediate (III), wherein the catalyst is Raney Nickle, palladium-carbon and platinum black, the molar ratio between reactant (II) and the catalyst is 1:(0.01-0.5), the reaction time is 0.5-10 hours; reacting the intermediate (III) with 2-methylsulfonyl-4-D,6-E-substituted pyrimidine for 0.5 - 20 hours in an organic solvent at a reaction temperature between room temperature and the boiling point of the solvent, to give 2-pyrimidinyloxy-$N$-aryl-benzylamine ($R^3$=H), wherein the molar ratio of the intermediate (III) to 2-methylsufonyl-4-d,6-E-substituted pyrimidine to base is 1:(1.0-1.2):(1-5), the said base is monovalent or divalent metal hydrides, alkoxides or carbonates, or organobase such as triethylamine and pyridine;
    reacting the mixture of the compound 2-pyrimidyloxy-$N$-aryl-benzylamine (I, $R^3$=H) shown by the above formula (I, $R^3$=H), an acid anhydride or an acid chloride $R^3$Cl (I, $R^3 \neq$H) and a base with a molar ratio of 1:(1.0-4.0):(0-2) for 2-8 hours under reflux condition, to form the compound as shown by formula (I) ($R^3 \neq$H), i.e., the acylated product (I, $R^3 \neq$H), wherein, the intermediates (II), (III) or the compound of formula (I) are shown by the following formulas:

UNITED STATES PATENT AND TRADEMARK OFFICE
CERTIFICATE OF CORRECTION

PATENT NO. : 6,800,590 B2
APPLICATION NO. : 10/380865
DATED : October 5, 2004
INVENTOR(S) : Lu et al.

It is certified that error appears in the above-identified patent and that said Letters Patent is hereby corrected as shown below:

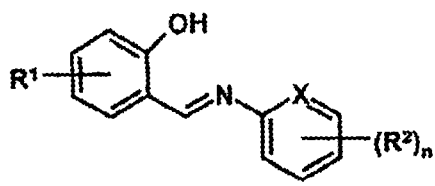

(II)

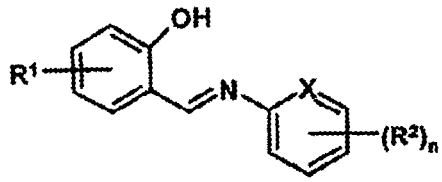

(III)

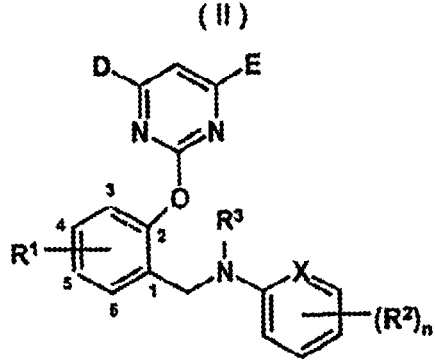

(I)

--

Signed and Sealed this

Eighteenth Day of March, 2008

JON W. DUDAS
*Director of the United States Patent and Trademark Office*